(12) United States Patent
Chen et al.

(10) Patent No.: US 10,550,210 B2
(45) Date of Patent: Feb. 4, 2020

(54) POLYISOCYANATES FROM FUSED BICYCLIC POLYOLS AND POLYURETHANES THEREFROM

(71) Applicant: Iowa State University Research Foundation, Inc., Ames, IA (US)

(72) Inventors: Jason Shih-Hao Chen, Ames, IA (US); Michael Richard Kessler, Pullman, WA (US); Michael Dennis Zenner, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 36 days.

(21) Appl. No.: 16/018,148

(22) Filed: Jun. 26, 2018

(65) Prior Publication Data

US 2018/0298023 A1 Oct. 18, 2018

Related U.S. Application Data

(62) Division of application No. 15/336,450, filed on Oct. 27, 2016, now Pat. No. 10,081,638, which is a division of application No. 14/434,710, filed as application No. PCT/US2013/064972 on Oct. 15, 2013, now Pat. No. 9,556,293.

(60) Provisional application No. 61/713,889, filed on Oct. 15, 2012, provisional application No. 61/872,116, filed on Aug. 30, 2013.

(51) Int. Cl.
| | |
|---|---|
| *C07D 493/04* | (2006.01) |
| *C08F 122/20* | (2006.01) |
| *C09J 4/00* | (2006.01) |
| *B60L 53/20* | (2019.01) |
| *C08G 18/32* | (2006.01) |
| *C08G 18/77* | (2006.01) |
| *C08L 75/08* | (2006.01) |
| *C09J 135/02* | (2006.01) |
| *H04B 3/54* | (2006.01) |

(52) U.S. Cl.
CPC ............ *C08F 122/20* (2013.01); *B60L 53/20* (2019.02); *C07D 493/04* (2013.01); *C08G 18/3218* (2013.01); *C08G 18/771* (2013.01); *C08L 75/08* (2013.01); *C09J 4/00* (2013.01); *C09J 135/02* (2013.01); *H04B 3/548* (2013.01); *C07C 2602/36* (2017.05); *C08L 2201/50* (2013.01); *H04B 2203/5425* (2013.01)

(58) Field of Classification Search
CPC .. C07C 265/14; C07C 2602/36; C07D 493/04
See application file for complete search history.

(56) References Cited

U.S. PATENT DOCUMENTS

| | | | |
|---|---|---|---|
| 4,013,688 A | 3/1977 | Babcock et al. | |
| 4,383,051 A * | 5/1983 | Meyborg | C08G 18/10 521/174 |
| 4,559,351 A | 12/1985 | Stoss et al. | |
| 4,791,156 A * | 12/1988 | Hostettler | C08G 18/42 433/199.1 |
| 6,737,481 B1 | 5/2004 | Kurian et al. | |
| 7,619,056 B2 * | 11/2009 | East | C07D 493/04 528/421 |
| 9,556,293 B2 | 1/2017 | Chen et al. | |
| 9,688,794 B2 | 6/2017 | Chen et al. | |
| 9,920,145 B2 | 3/2018 | Chen et al. | |
| 10,081,638 B2 | 9/2018 | Chen et al. | |
| 10,280,241 B2 | 5/2019 | Chen et al. | |
| 10,392,471 B2 | 8/2019 | Chen et al. | |
| 2001/0023276 A1 | 9/2001 | Schoenfeld | |
| 2003/0212244 A1 | 11/2003 | Hayes et al. | |
| 2009/0018300 A1* | 1/2009 | Bloom | C08G 61/12 527/102 |
| 2012/0071577 A1 | 3/2012 | Pfeffer et al. | |
| 2012/0073472 A1 | 3/2012 | Spyrou et al. | |
| 2014/0249285 A1* | 9/2014 | Palmese | C08F 224/00 526/268 |
| 2015/0274861 A1 | 10/2015 | Chen et al. | |
| 2015/0274880 A1 | 10/2015 | Chen et al. | |
| 2016/0289218 A1 | 10/2016 | Chen et al. | |
| 2016/0333143 A1 | 11/2016 | Chen | |
| 2017/0044178 A1 | 2/2017 | Chen | |
| 2017/0226243 A1 | 8/2017 | Chen et al. | |
| 2018/0148524 A1 | 5/2018 | Chen et al. | |

FOREIGN PATENT DOCUMENTS

| | | |
|---|---|---|
| CN | 1384109 A | 12/2002 |
| CN | 103044669 A | 4/2013 |
| DE | 102007006442 A1 | 8/2008 |
| EA | 000565 B1 | 12/1999 |
| EP | 0114270 A1 | 8/1984 |
| GB | 985614 | 3/1965 |
| JP | 2002265419 A | 9/2002 |
| KR | 20130070970 A | 6/2013 |
| WO | WO-9636639 A1 | 11/1996 |
| WO | WO-9702307 A1 | 1/1997 |
| WO | WO-0108677 A1 | 2/2001 |
| WO | WO-2004098538 A2 | 11/2004 |
| WO | WO-2010138842 A1 | 12/2010 |
| WO | WO-2013066461 A2 | 5/2013 |
| WO | WO-2014062625 A1 | 4/2014 |
| WO | WO-2014062631 A1 | 4/2014 |

OTHER PUBLICATIONS

Bachmann, Macromol. Chem. Phys. 2001, 202, 3410-3419 (Year: 2001).*

(Continued)

*Primary Examiner* — Robert C Boyle

(74) *Attorney, Agent, or Firm* — Schwegman Lundberg & Woessner, P.A.

(57) ABSTRACT

The present invention is directed to polyisocyanates and polyurethanes derived therefrom. In various embodiments, the present invention provides polyisocyanates, methods of making the polyisocyanates from fused bicyclic alcohols, polyurethanes, and methods of making the polyurethanes from the polyisocyanates.

20 Claims, No Drawings

(56) References Cited

OTHER PUBLICATIONS

"U.S. Appl. No. 15/153,234, Notice of Allowance dated Apr. 10, 2019", 8 pgs.
"U.S. Appl. No. 15/153,234, Response filed Mar. 20, 2019 to Final Office Action dated Jan. 24, 2019", 10 pgs.
"U.S. Appl. No. 15/881,117, Notice of Allowability dated Mar. 14, 2019", 2 pgs.
"U.S. Appl. No. 15/881,117, Notice of Allowance dated Feb. 20, 2019", 9 pgs.
"U.S. Appl. No. 15/153,234, Final Office Action dated Jan. 24, 2019", 7 pgs.
"U.S. Appl. No. 15/153,234, Non Final Office Action dated Oct. 10, 2018", 9 pgs.
"U.S. Appl. No. 15/153,234, Response filed Jan. 4, 2019 to Non Final Office Action dated Oct. 10, 2018", 19 pgs.
"U.S. Appl. No. 15/153,234, Response filed Sep. 10, 2018 to Restriction Requirement dated Aug. 31, 2018", 18 pgs.
"U.S. Appl. No. 15/153,234, Restriction Requirement dated Aug. 31, 2018", 7 pgs.
"U.S. Appl. No. 14/434,710, Notice of Allowance dated Sep. 21, 2016", 9 pgs.
"U.S. Appl. No. 14/434,710, Response filed Aug. 24, 2016 to Restriction Requirement dated Jul. 6, 2016", 12 pgs.
"U.S. Appl. No. 14/434,710, Restriction Requirement dated Jul. 6, 2016", 10 pgs.
"U.S. Appl. No. 14/434,719, Notice of Allowability dated Apr. 4, 2017", 5 pgs.
"U.S. Appl. No. 14/434,719, Notice of Allowance dated Mar. 23, 2017", 11 pgs.
"U.S. Appl. No. 14/434,719, Response filed Oct. 11, 2016 to Restriction Requirement dated Aug. 25, 2016", 13 pgs.
"U.S. Appl. No. 14/434,719, Restriction Requirement dated Aug. 25, 2016", 8 pgs.
"U.S. Appl. No. 15/336,450, Non Final Office Action dated Feb. 15, 2018", 8 pgs.
"U.S. Appl. No. 15/336,450, Notice of Allowance dated Jun. 15, 2018", 8 pgs.
"U.S. Appl. No. 15/336,450, Response Filed May 11, 2018 to Non Final Office Action dated Feb. 15, 2018", 8 pgs.
"U.S. Appl. No. 15/581,229, Notice of Allowance dated Nov. 24, 2017", 9 pgs.
"U.S. Appl. No. 15/581,229, Preliminary Amendment filed May 1, 2017", 12 pgs.
"U.S. Appl. No. 15/881,117, Preliminary Amendment filed Jan. 29, 2018", 14 pgs.
"Application Serial No. Preliminary Amendment filed Apr. 9, 2015", 13 pgs.
"International Application Serial No. PCT/US2013/064960, International Preliminary Report on Patentability dated Apr. 30, 2015", 12 pgs.
"International Application Serial No. PCT/US2013/064960, International Search Report dated Feb. 4, 2014", 8 pgs.
"International Application Serial No. PCT/US2013/064960, Written Opinion dated Feb. 4, 2014", 10 pgs.
"International Application Serial No. PCT/US2013/064972, International Preliminary Report on Patentability dated Apr. 30, 2015", 10 pgs.
"International Application Serial No. PCT/US2013/064972, International Search Report dated Feb. 4, 2014", 5 pgs.
"International Application Serial No. PCT/US2013/064972, Written Opinion dated Feb. 4, 2014", 8 pgs.
Bachmann, Frank, et al., "Synthesis of Novel Polyurethanes and Polyureas by Polyaddition Reactions of Dianhydrohexitol Configurated Diisocyanates", Macromol. Chem. Phys., vol. 202, No. 17, (Jan. 1, 2001), 3410-3419.
Barros, Thalita G, et al., "Novel Peptide Mimetics Based on N-protected Amino Acids Derived from Isomannide as Potential Inhibitors of NS3 Serine Protease of Hepatitis C Virus", Letters in Organic Chemistry, vol. 9, No. 4, (Feb. 1, 2012), 239-249.

Beldi, M., et al., "Characterization of cyclic and non-cyclic poly-(ether-urethane)s bio-based sugar diols by a combination of MALDI-TOF and NMR", European Polymer Journal, 43, (2007), 3415-3433.
Cocker, J. D, et al., "Action of some steroids on the central nervous system of the mouse. I. Synthetic methods", Journal of Medicinal Chemistry 8(4), (1965).
Feng, Xianhong, et al., "Overview of advances in sugar-based polymers", Polymers for Advanced Technologies, vol. 22, No. 1, (Jan. 10, 2011), 139-150.
Garaleh, Mazen, et al., "(Co-)Polyesters Derived from Isosorbide and 1,4-Cyclohexane Dicarboxylic Acid and Succinic Acid", Macromol. Chem. Phys., 211, (2010), 1206-1214.
Gohil, R. M., "Properties and Strain Hardening Character of Polyethylene Terephthalate Containing Isosorbide", Polymer Engineering and Science, (2009), 544-553.
Hojabri, Leila, et al., "Fatty Acid-Derived Diisocyanate and Biobased Polyurethane Produced from Vegetable Oil: Synthesis, Polymerization, and Characterization", Biomacromolecules, 10, (1009), 884-891.
Hojabri, Leila, et al., "Novel Long Chain Unsaturated Diisocyanate from Fatty Acid: Synthesis, Characterization, and Application in Bio-Based Polyurethane", Journal of Polymer Science: Part A: Polymer Chemistry, 48, (2010), 3302-3310.
Imm, Sebastian, et al., "Improved Ruthenium-Catalyzed Amination of Alcohols with Ammonia: Synthesis of Diamines and Amino Esters", Angew, Chem. Int. Ed., 50, (2011), 7599-7603.
Lee, Chi-Han, et al., "Synthesis, Characterization, and Properties of Polyurethanes Containing 1,4:3,6-Dianhydro-D-sorbitol", Journal of Polymer Science: Part A: Polymer Chemistry, 47, (2009), 6025-6031.
Li, Ruilin, et al., "Synthesis and antifertility activities of A-norsteroidal compounds", Yiyao Gongye, 17(9), (1987).
Marin, Romina, et al., "Carbohydrate-Based Poly(ester-urethane)s: A Comparative Study Regarding Cyclic Alditols Extenders and Polymerization Procedures", Journal of Applied Polymer Science, 114, (2009), 3723-3736.
Min, Zhen Li, et al., "Asymmetric synthesis of 3-butylphthalide using isomannide and isosorbide as chiral auxiliaries", Chinese Chemical Letters, vol. 18, No. 11, (Nov. 5, 2007), 1361-1363.
Nakamura, Yoshinobu, et al., "Effects of the Compatibility of a Polyacrylic Block Copolymer/Tackifier Blend on the Phase Structure and Tack of a Pressure-Sensitive Adhesive", Journal of Applied Polymer Science, vol. 123, No. 5, (Mar. 5, 2012), 2883-2893.
Rose, Marcus, et al., "Isosorbide as a Renewable Platform chemical for Versatile Applications—Quo Vadis?", ChemSusChem, 5, (2012), 167-176.
Sabiong, Rafaei, et al., "Incorporation of Isosorbide into Poly(butyiene terephthalate) via Solid-State Polymerization", Macromolecules, American Chemical Society, vol. 9, (Nov. 10, 2008), 3090-3097.
Scalia, Santo, et al., "HPLC determination of ursodeoxycholic acid disuccinate in tablet formulations", (1991), 2 pgs.
Thiem, Joachim, et al., "Synthesis and properties of polyurethanes derived from diaminodianhydroalditols", Makromol. Chem., 187, (1986), 2775-2785.
Varkey, Elizabeth Chirackal, et al., "Isosorbide based chiral polyurethanes: optical and thermal studies", Journal of Materials Science, vol. 45, No. 7, (Jan. 13, 2010), 1912-1920.
Zenner, Michael D, et al., "Polyurethanes from Isosorbide-Based Diisocyanates", ChemSusChem, 6, (2013), 1182-1185.
"U.S. Appl. No. 15/085,345, Non Final Office Action dated Nov. 27, 2017", 9 pgs.
"U.S. Appl. No. 15/085,345, Notice of Allowance dated May 30, 2018", 12 pgs.
"U.S. Appl. No. 15/085,345, Response filed Feb. 27, 2018 to Non Final Office Action dated Nov. 27, 2017", 13 pgs.
"U.S. Appl. No. 15/085,345, Response filed Sep. 25, 2017 to Restriction Requirement dated Jul. 27, 2017", 10 pgs.
"U.S. Appl. No. 15/085,345, Restriction Requirement dated Jul. 27, 2017", 9 pgs.
Chen, "Bio-based polymeric materials from vegetable oils", PhD thesis, Iowa State University, (Oct. 2014).

(56) References Cited

OTHER PUBLICATIONS

Chen, Po-Cheng, et al., "New Crosslinked Polymer from a Rapid Polymerization of Acrylic Acid with Triaziridine-Containing Compounds", Journal of Applied Polymer Science, vol. 104, (2007), 809-815.
Ligadas, et al., "Renewable polymeric materials from vegetable oils: a perspective", Material stoday, vol. 16, issue 9, (Sep. 2013), 337-343.
Schoenfeld, Uwe, "Polymer Material", patsnap, EA000565B1; Publication No.=EA000565B1; Application No.=EA980004AAssignee, Abstract Only; Assignee Name—Preform Raumgliederungssysteme Gmbh, DE.; Priority Data: 19524514 Jul. 1995 DE; 9601243 Jul. 5, 1996.
Stemmelen, M., et al., "A Fully Biobased Epoxy Resin from Vegetable Oils: From the Synthesis of the Precursors by Thiol-ene Reaction to the Study of the Final Material", accepted Mar. 14, 2011; DOI: 10. 1002/pola.24674; Published online Apr. 8, 2011 in Wiley Online Library (wileyonlinelibrary.com)., wileyonlinelibrary.com/journal/jpola, (Apr. 8, 2011), 2434-2444.
Xia, et al., "Castor-Oil-Based Waterborne Polyurethane Dispersions Cured with an Aziridine-Based Crosslinker", Macromol. Mater. Eng., (Apr. 2011), 703-709.

\* cited by examiner

POLYISOCYANATES FROM FUSED BICYCLIC POLYOLS AND POLYURETHANES THEREFROM

CROSS-REFERENCE TO RELATED APPLICATIONS

This application is a divisional of U.S. patent application Ser. No. 15/336,450, filed Oct. 27, 2016, which is a divisional of U.S. patent application Ser. No. 14/434,710, filed Apr. 9, 2015, which is a U.S. National Stage Filing under 35 U.S.C. 371 from International Application No. PCT/US2013/064972, filed on 15 Oct. 2013 and published as WO 2014/062631 on 24 Apr. 2014, which claims the benefit of priority to U.S. Provisional Patent Application Ser. No. 61/713,889 entitled "POLYISOCYANATES FROM FUSED BICYCLIC POLYOLS AND POLYURETHANES THEREFROM," filed Oct. 15, 2012, and also claims the benefit of priority to U.S. Provisional Patent Application Ser. No. 61/872,116 entitled "TACKIFIER COMPOUNDS AND METHODS OF USING THE SAME." filed Aug. 30, 2013, which applications and publications are incorporated herein in their entirety by reference.

BACKGROUND OF THE INVENTION

Polyurethanes are a versatile class of polymers that are used in a wide range of applications, for example: plastics, elastomers, flexible or rigid foams, gaskets and seals, coatings, fibers, and adhesives. Polyurethanes can be made by combining polyols and polyisocyanates, such as diisocyanates, optionally including chain-extenders such as diols, diamines, and the like. Polyols and polyisocyanates are typically derived from petroleum-based materials. There has been work in recent years to replace the petroleum-derived polyols with polyols derived from non-petroleum sources, such as vegetable oil, soybean oil, and castor oil. However, little attention has been paid to development of polyisocyanates from renewable non-petroleum sources.

SUMMARY OF THE INVENTION

The present invention is directed to polyisocyanates derived from fused bicyclic alcohols, such as isosorbides, and polyurethanes derived therefrom.

In various embodiments, the polyisocyanates and polyurethanes of the present invention have advantages over other polyisocyanates and polyurethanes, some of which are unexpected. Past attempts to convert fused bicyclic alcohols into a biorenewable polyisocyanates have either been low-yielding or required a relatively large amount of expensive catalysts; however, various embodiments of the present method of preparing a polyisocyanate from a fused polyol and an acid anhydride can be more environmentally friendly (e.g. benign) and cost effective.

The present invention provides novel polyisocyanates and polyurethanes derived therefrom. In some examples, the polyisocyanates are advantageously derived primarily from non-petroleum based materials. In some embodiments, the polyisocyanates can be made using environmentally-friendly techniques, with some or all synthetic steps avoiding or limiting at least one of wasted materials, wasted energy, and the use of toxic or petroleum-derived reagents. In some examples, the polyisocyanates of the present invention can be made at lower cost than other polyisocyanates. In some embodiments, time-consuming purification procedures such as chromatography can be avoided and instead crude material can be used in subsequent steps or facile and easily scalable vacuum distillation can be used for purification. In various embodiments, the polyurethanes of the present invention can form aqueous dispersions more effectively than other polyurethanes, allowing the application of polyurethanes without the use of or with reduced use of environmentally harmful and toxic volatile organic solvents.

In various embodiments, the polyisocyanates can be used to generate polyurethanes using a more environmentally-friendly synthesis and using less toxic materials than polyurethanes made from other polyisocyanates. In some examples, the polyisocyanates of the present invention can be used to synthesize polyurethanes at lower cost than polyurethanes synthesized from other polyisocyanates. The polyurethanes of the present invention can have characteristics that advantageously distinguish over other polyurethanes, including at least one of better strength, better rigidity, better melting properties, more biorenewably derived, greater biodegradability, better ability to form aqueous dispersions, and lower cost. For example, in various embodiments, the fused cyclic polyisocyanates can provide polyurethanes that are more rigid than other non-cyclic isocyanates, including those derived from fatty acids.

In various embodiments, the present invention provides a compound of Formula (I):

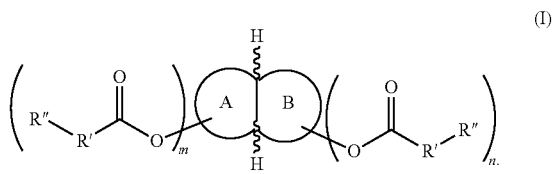

In Formula (I), fused rings A and B are each independently selected from ($C_5$-$C_{10}$)cycloalkyl and ($C_2$-$C_{10}$)heterocyclyl. The variables m and n are each independently 1-8. The variable R' is selected from the group consisting of ($C_2$-$C_{10}$) alkanylene, ($C_2$-$C_{10}$)alkenylene, and ($C_2$-$C_{10}$)alkynylene, and R' is unsubstituted or substituted with at least one J. The variable R" is selected from the group consisting of —C(O) OH, —C(O)O$^-$X$^+$, —C(O)F, —C(O)Cl, —C(O)Br, —C(O) I, —C(O)N$_3$, and —NCO, wherein X$^+$ is a counterion. In Formula (I), fused rings A and B are each independently unsubstituted or substituted with at least one of J, ($C_1$-$C_{10}$) alkyl, ($C_2$-$C_{10}$)alkenyl, ($C_2$-$C_{10}$)alkynyl, ($C_1$-$C_{10}$)haloalkyl, ($C_1$-$C_{10}$)alkoxy, ($C_1$-$C_{10}$)haloalkoxy, ($C_1$-$C_{10}$)cycloalkyl ($C_0$-$C_{10}$)alkyl, ($C_1$-$C_{10}$)heterocyclyl($C_0$-$C_{10}$)alkyl, ($C_1$-$C_{10}$) aryl($C_0$-$C_{10}$)alkyl, or ($C_1$-$C_{10}$)heteroaryl($C_0$-$C_{10}$)alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J. In Formula (I), J independently at each occurrence is selected from the group consisting of F, Cl, Br, I, OR, CN, CF$_3$, OCF$_3$, R, O, S, C(O), S(O), methylenedioxy, ethylenedioxy, N(R)$_2$, SR, S(O)R, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-2}$NHC(O)R, N(R)N(R)C(O)R, N(R)N(R)C(O)OR, N(R)N(R)C(O)N(R)$_2$, N(R)SO$_2$R, N(R)SO$_2$N(R)$_2$, N(R)C (O)OR, N(R)C(O)R, N(R)C(S)R, N(R)C(O)N(R)$_2$, N(R)C (S)N(R)$_2$, N(C(O)R)C(O)R, N(OR)R, C(=NH)N(R)$_2$, C(O)N(OR)R, and C(=NOR)R, wherein R is independently at each occurrence selected from the group consisting of hydrogen, ($C_1$-$C_{10}$)alkyl, ($C_1$-$C_{10}$)cycloalkyl, ($C_1$-$C_{10}$)cycloalkyl($C_1$-$C_{10}$)alkyl, ($C_1$-$C_{10}$)aryl, ($C_1$-$C_{10}$)aralkyl, ($C_1$-

$C_{10}$)heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

In various embodiments, the present invention provides a method of making a polyisocyanate. The method includes contacting a compound having the structure

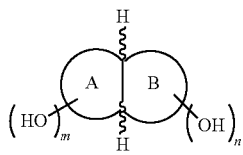

and an acid anhydride having the structure

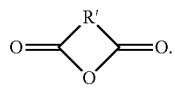

The contacting of the compound and the acid anhydride provides a polyacid having the structure of Formula (I)

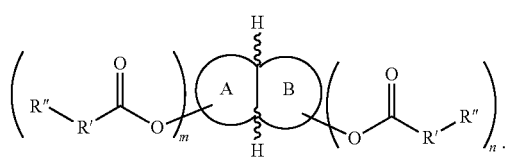

In the structure of Formula (I), R" is —C(O)OH. The method also includes contacting the polyacid and an acyl halide generator. Contacting the polyacid and the acyl halide generator provides a polyacid halide having the structure of Formula (I) where R" is —C(O)X, wherein X is halide. The method also includes contacting the polyacid halide and an azide generator under conditions suitable to provide a polyisocyanate having the structure of Formula (I) where R" is —NCO. In the structure of Formula (I), fused rings A and B are each independently selected from $(C_5-C_{10})$cycloalkyl and $(C_2-C_{10})$heterocyclyl. The variables m and n are each independently 1-8. The variable R' is selected from the group consisting of $(C_2-C_{10})$alkanylene, $(C_2-C_{10})$alkenylene, and $(C_2-C_{10})$alkynylene, where R' is unsubstituted or substituted with at least one J. In the structure of Formula (I), fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J. In Formula (I), J independently at each occurrence is selected from the group consisting of F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, C(O)N(R)_2, OC(O)N(R)_2, C(S)N(R)_2, $(CH_2)_{0-2}$NHC(O)R, N(R)N(R)C(O)R, N(R)N(R)C(O)OR, N(R)N(R)C(O)N(R)_2, $N(R)SO_2R$, $N(R)SO_2N(R)_2$, N(R)C(O)OR, N(R)C(O)R, N(R)C(S)R, N(R)C(O)N(R)_2, N(R)C(S)N(R)_2, N(C(O)R)C(O)R, N(OR)R, C(=NH)N(R)_2, C(O)N(OR)R, and C(=NOR)R, wherein R is independently at each occurrence selected from the group consisting of hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

In various embodiments, the present invention provides a polyurethane comprising a plurality of subunits each having the structure of Formula (II)

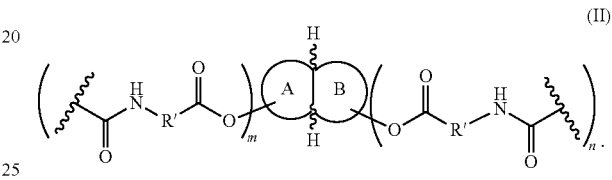

In Formula (II), fused rings A and B are each independently selected from $(C_5-C_{10})$cycloalkyl and $(C_2-C_{10})$heterocyclyl. The variables m and n are each independently 1-8. The variable R' is selected from the group consisting of $(C_2-C_{10})$alkanylene, $(C_2-C_{10})$alkenylene, and $(C_2-C_{10})$alkynylene, where R' is unsubstituted or substituted with at least one J. In Formula (II), fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; where each alkyl, alkenyl, alkynyl, haloalkyl, alkoxy, haloalkoxy, cycloalkyl, aryl, heterocyclyl, and heteroaryl is independently unsubstituted or further substituted with at least one J. In Formula (II), J independently at each occurrence is selected from the group consisting of F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, C(O)N(R)_2, OC(O)N(R)_2, C(S)N(R)_2, $(CH_2)_{0-2}$NHC(O)R, N(R)N(R)C(O)R, N(R)N(R)C(O)OR, N(R)N(R)C(O)N(R)_2, $N(R)SO_2R$, $N(R)SO_2N(R)_2$, N(R)C(O)OR, N(R)C(O)R, N(R)C(S)R, N(R)C(O)N(R)_2, N(R)C(S)N(R)_2, N(C(O)R)C(O)R, N(OR)R, C(=NH)N(R)_2, C(O)N(OR)R, and C(=NOR)R, where R is independently at each occurrence selected from the group consisting of hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values, and the endpoints of any sequence or range, is also disclosed.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as alkoxy groups, aryloxy groups, aralkyloxy groups, oxo(carbonyl) groups, carboxyl groups including carboxylic acids, carboxylates, and carboxylate esters; a sulfur-containing group such as alkyl and aryl sulfide groups; and other heteroatom-containing groups. Non-limiting examples of organic groups include OR', OC(O)N(R')$_2$, CN, CF$_3$, OCF$_3$, R', C(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen (in examples that include other carbon atoms) or a carbon-based moiety, and wherein the carbon-based moiety can itself be further substituted; for example, wherein R' can be hydrogen (in examples that include other carbon atoms), alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl, or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J. Examples of organic groups include linear and/or branched groups such as alkyl groups, fully or partially halogen-substituted haloalkyl groups, alkenyl groups, alkynyl groups, aromatic groups, acrylate functional groups, and methacrylate functional groups; and other organic functional groups such as ether groups, cyanate ester groups, ester groups, carboxylate salt groups, and masked isocyano groups. Examples of organic groups include, but are not limited to, alkyl groups such as methyl, ethyl, propyl, isopropyl, n-butyl, s-butyl, and t-butyl groups, acrylate functional groups such as acryloyloxypropyl groups and methacryloyloxypropyl groups; alkenyl groups such as vinyl, allyl, and butenyl groups; alkynyl groups such as ethynyl and propynyl groups; aromatic groups such as phenyl, tolyl, and xylyl groups; cyanoalkyl groups such as cyanoethyl and cyanopropyl groups; halogenated hydrocarbon groups such as 3,3,3-trifluoropropyl, 3-chloropropyl, dichlorophenyl, and 6,6,6,5,5,4,4,3,3-nonafluorohexyl groups; alkenyloxypoly(oxyalkyene) groups such as allyloxy(polyoxyethylene), allyloxypoly(oxypropylene), and allyloxy-poly(oxypropylene)-co-poly(oxyethylene) groups; alkyloxypoly(oxyalkyene) groups such as propyloxy(polyoxyethylene), propyloxypoly(oxypropylene), and propyloxy-poly(oxypropylene)-co-poly(oxyethylene) groups; halogen substituted alkyloxypoly(oxyalkyene) groups such as perfluoropropyloxy(polyoxyethylene), perfluoropropyloxypoly(oxypropylene), and perfluoropropyloxy-poly(oxypropylene)-co-poly(oxyethylene) groups; alkoxy groups such as methoxy, ethoxy, n-propoxy, isopropoxy, n-butoxy, and ethylhexyloxy groups; aminoalkyl groups such as 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole groups; epoxyalkyl groups such as 3-glycidoxypropyl, 2-(3,4,-epoxycyclohexyl)ethyl, and 5,6-epoxyhexyl groups; ester functional groups such as actetoxyethyl and benzoyloxypropyl groups; hydroxy functional groups such as 2-hydroxyethyl groups; masked isocyanate functional groups such as propyl-t-butylcarbamate, and propylethylcarbamate groups; aldehyde functional groups such as undecanal and butyraldehyde groups; anhydride functional groups such as 3-propyl succinic anhydride and 3-propyl maleic anhydride groups; and metal salts of carboxylic acids such as the zinc, sodium, or potassium salts of 3-carboxypropyl and 2-carboxyethyl.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule, or onto an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl group are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a Ca-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazoyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-11-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

The terms "halo" or "halogen" or "halide", as used herein, by themselves or as part of another substituent mean, unless otherwise stated, a fluorine, chlorine, bromine, or iodine atom, preferably, fluorine, chlorine, or bromine.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "independently selected from" as used herein refers to referenced groups being the same, different, or a mixture thereof, unless the context clearly indicates otherwise. Thus, under this definition, the phrase "X$^1$, X$^2$, and X$^3$ are independently selected from noble gases" would include the scenario where, for example, X$^1$, X$^2$, and X$^3$ are all the same, where X$^1$, X$^2$, and X$^3$ are all different, where X$^1$ and X$^2$ are the same but X$^3$ is different, and other analogous permutations.

The term "room temperature" as used herein refers to ambient temperature, which can be, for example, between about 15° C., and about 28° C.

The term "polyisocyanate" as used herein refers to a compound having more than one isocyanate moiety, for example, a diisocyanate, triisocyanate, tetraisocyanate, and the like.

The term "polyol" as used herein refers to a compound having more than one alcohol moiety, for example, a diol, triol, tetraol, and the like.

The term "polyurethane" as used herein refers to a polymer including a repeating unit that includes a carbamate moiety. e.g., —OC(O)—NH—.

Compound of Formula (I).

In various embodiments, the present invention provides a compound of Formula (I):

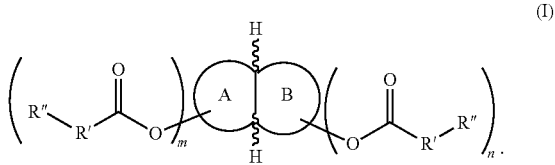

Formula (I) includes fused rings A and B, which share a single carbon-carbon bond. Rings A and B can be the same or different, and are each independently selected from (C$_5$-C$_{10}$)cycloalkyl and (C$_2$-C$_{10}$)heterocyclyl, wherein the designated number of carbon atoms includes the two carbon atoms that are shared by rings A and B. In some examples, rings A and B can be the same size, and can both be cyclopentyl, cyclohexyl, cyclopentyl, cyclooctyl, cyclononyl, or cyclodecyl. The two hydrogen atoms at the points of fusion can have any suitable stereochemical configuration with respect to each other and with respect to other functional groups on rings A and B, and can be syn or anti.

Rings A and B can have any suitable number and variety of functional groups thereon. Rings A and B each include one or more ester substituents having the formula R"—R'—C(O)O—. The variables m and n are each independently 1-8; thus, Rings A and B can each independently have about 1 to 8 ester substituents thereon. The variables m and n can have different values, or the variable m and n can be equal. The variables m and n can each be 1. Rings A and B can each have the same type and number of ester substituents or a different type and number of ester substituents. Rings A and B each have at least one ester substituent. In some examples, fused rings A and B can be each independently unsubstituted with the exception of the ester substituents having the formula R"—R'—C(O)O—.

In some examples, fused rings A and B can be each independently substituted with at least one of J, (C$_1$-C$_{10}$)alkyl, (C$_2$-C$_{10}$)alkenyl, (C$_2$-C$_{10}$)alkynyl, (C$_1$-C$_{10}$)haloalkyl, (C$_1$-C$_{10}$)alkoxy. (C$_1$-C$_{10}$)haloalkoxy, (C$_1$-C$_{10}$)cycloalkyl (C$_0$-C$_{10}$)alkyl, (C$_1$-C$_{10}$)heterocyclyl(C$_0$-C$_{10}$)alkyl, (C$_1$-C$_{10}$)aryl(C$_0$-C$_{10}$)alkyl, or (C$_1$-C$_{10}$)heteroaryl(C$_0$-C$_{10}$)alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J. The variable J independently at each occurrence is selected from the group consisting of F, Cl, Br, I, OR, CN, CF$_3$, OCF$_3$, R, O, S, C(O), S(O), methylenedioxy, ethylenedioxy, N(R)$_2$, SR, S(O)R, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-2}$NHC(O)R, N(R)N(R)C(O)R, N(R)N(R)C(O)OR, N(R)N(R)C(O)N(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(C(O)R)C(O)R, N(OR)R, C(=NH)N(R)$_2$, C(O)N(OR)R, and C(=NOR)R, wherein R is independently at each occurrence selected from the group consisting of hydrogen, (C$_1$-C$_{10}$)alkyl, (C$_1$-C$_{10}$)cycloalkyl, (C$_1$-C$_{10}$)cycloalkyl(C$_1$-C$_{10}$)alkyl, (C$_1$-C$_{10}$)aryl, (C$_1$-C$_{10}$)aralkyl, (C$_1$-C$_{10}$)heterocyclyl, (C$_1$-C$_{10}$)heterocyclyl(C$_1$-C$_{10}$)alkyl, (C$_1$-C$_{10}$)heteroaryl, and (C$_1$-C$_{10}$)heteroaryl(C$_1$-C$_{10}$)alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

In Formula (I), the variable R' in the ester substituent is selected from the group consisting of (C$_2$-C$_{10}$)alkanylene, (C$_2$-C$_{10}$)alkenylene, and (C$_2$-C$_{10}$)alkynylene. In some examples, R' can be unsubstituted, and in other examples, R' can be substituted with at least one J, as defined herein. In various examples, R' can be ethanylene (—CH$_2$—CH$_2$—), propanylene (—CH$_2$—CH$_2$—CH$_2$—), or butanylene (—CH$_2$—CH$_2$—CH$_2$—CH$_2$—).

In Formula (I), the variable R" is selected from the group consisting of —C(O)OH, —C(O)O$^-$X$^+$, —C(O)F, —C(O)Cl, —C(O)Br, —C(O)I, —C(O)N$_3$, and —NCO, wherein X$^+$ is a counterion; thus, in embodiments where m=n=1, Formula (I) can represent a diacid, a diacid salt, a diacyl fluoride, a diacyl chloride, a diacyl bromide, a diacyl iodide, a diacyl azide, or a diisocyanate, respectively. The variable X$^+$ can be any suitable counterion bearing a +1 charge. For example, X$^+$ can be a group I element such as Na$^+$ or K$^+$, Ag$^+$, or NH$_4^+$. In some embodiments, multiple —O$^-$ groups can have a single counterion having a greater than +1 charge, for example Al$^{3+}$, Ca$^{2+}$, Cu$^{2+}$, Fe$^{2+}$, Fe$^{3+}$, or Mg$^{2+}$. In some embodiments, R"=—NCO and Formula (I) represents a polyisocyanate.

In some embodiments, at least one of the ester substituents having the formula R"—R'—C(O)O— is alpha to a carbon atom shared by rings A and B, for example, R"—R'—C(O)O— is bound to an atom of ring A or B that is bound to a carbon atom shared by rings A and B. In some examples, at least one ester substituent having the formula R"—R'—C(O)O— on each of rings A and B is alpha to a carbon atom shared by rings A and B. In some examples, an ester substituent having the formula R"—R'—C(O)O— on ring A is alpha to a carbon atom shared by rings A and B, and an ester substituent having the formula R"—R'—C(O)O— on ring B is alpha to the other carbon atom shared by rings A and B. and m can equal n or both m and n can equal 1.

In some examples, at least one of rings A and B include at least one oxygen atom. In some embodiments, each of rings A and B include at least one oxygen atom. In some examples, each of rings A and B is a tetrahydrofuran ring (e.g. cyclotetramethylene oxide, having any suitable substituents), where each of the two carbon atoms shared by rings A and B is alpha to the oxygen atom in at least one of rings A and B. In some examples, each of rings A and B is a tetrahydrofuran ring, where one the two carbon atoms shared by rings A and B is alpha to the oxygen atom in ring A, and the other carbon atom shared by rings A and B is alpha to the oxygen atom in ring B.

In some embodiments, m and n are 1, and each of rings A and B includes at least one oxygen atom, such that one the two carbon atoms shared by rings A and B is alpha to the at least one oxygen atom in ring A and alpha to the ester substituent having the formula R"—R'—C(O)O— substituted on ring B, and the other carbon atom shared by rings A and B is alpha to the at least one oxygen atom in ring B and alpha to the ester substituent having the formula R"—R'—C(O)O— substituted on ring A.

In various embodiments, the compound of Formula (I) is a diisocyanate having the following structure:

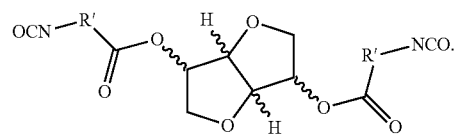

In various embodiments, the compound of Formula (I) is a diisocyanate having the following system, having the structure:

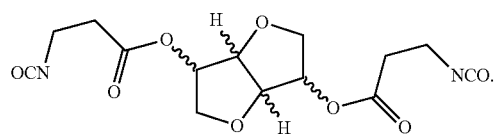

In various embodiments, the compound of Formula (I) is a diisocyanate having a fused bicyclic tetrahydrofuran ring system with the stereochemistry of an isosorbide ring system, having the structure:

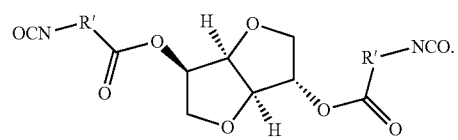

In various embodiments, the compound of Formula (I) is a diisocyanate having a fused bicyclic tetrahydrofuran ring system with the stereochemistry of an isosorbide ring system, where R' is ethanylene, having the structure:

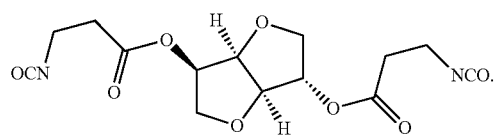

In various embodiments, the compound of Formula (I) is a diisocyanate having a fused bicyclic tetrahydrofuran ring system with the stereochemistry of an isomannide ring system, having the structure:

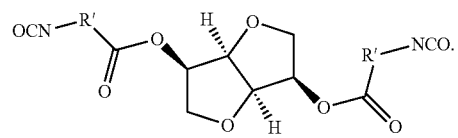

In various embodiments, the compound of Formula (I) is a diisocyanate having a fused bicyclic tetrahydrofuran ring system with the stereochemistry of an isomannide ring system, where R' is ethanylene, having the structure:

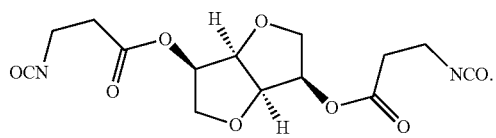
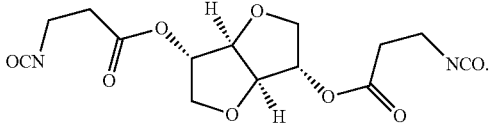

In various embodiments, the compound of Formula (I) is a diisocyanate having a fused bicyclic tetrahydrofuran ring system with the stereochemistry of an isoidide ring system, having the structure:

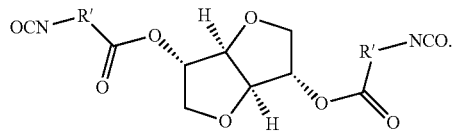

In various embodiments, the compound of Formula (I) is a diisocyanate having a fused bicyclic tetrahydrofuran ring system with the stereochemistry of an isoidide ring system, where R' is ethanylene, having the structure:

Method of Making a Polyisocyanate.

In various embodiments, the present invention provides a method of making the compound of Formula (I). The present invention provides embodiments of both the compound of Formula (I) and also a method of making the compound of Formula (I) that encompass any suitable method of making the compound of Formula (I); the compound of Formula (I) is to be understood as not limited by any particular method of making the compound.

In some examples, in the compound of Formula (I) R" is —NCO, and the present invention provides a method of making a polyisocyanate. In some examples, in the compound of Formula (I) R" is —NCO, and the variables m and n are 1, and the present invention provides a method of making a method of making a diisocyanate.

An example embodiment of the method of the present invention, wherein the fused bicyclic polyol is isosorbide, is shown in Scheme 1.

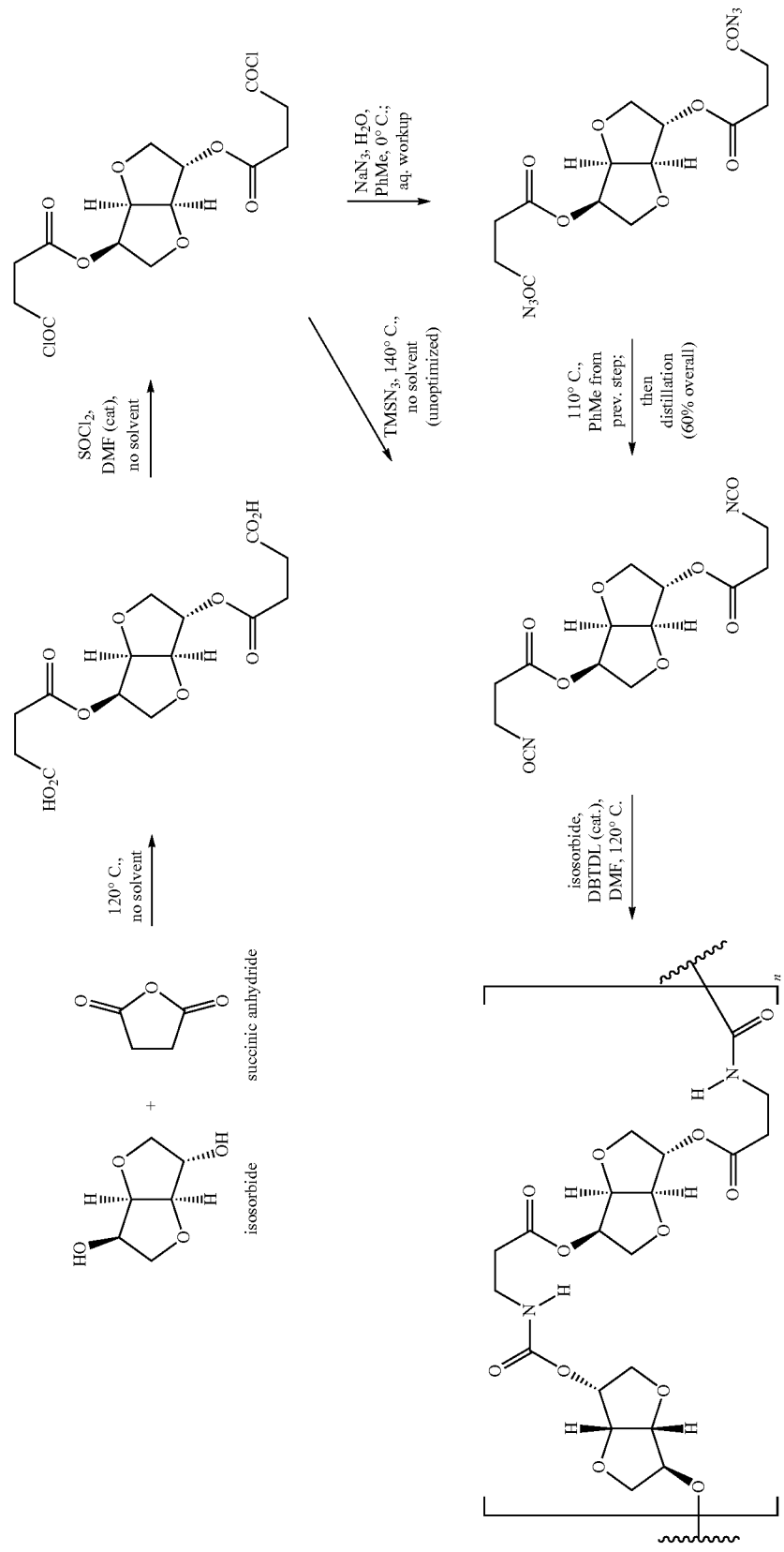

The method can include contacting a fused bicyclic polyol and an acid anhydride to provide a polyacid, such as a diacid. The fused bicyclic polyol can have the structure:

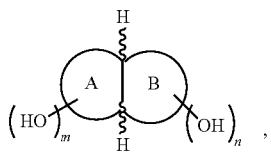

wherein rings A and B are analogous to rings A and B as described herein for Formula (I), except that the ester groups of Formula (I). R"—R'—C(O)O—, are hydroxyl groups, —OH. Thus, as with Formula (I), fused rings A and B are each independently selected from ($C_5$-$C_{10}$)cycloalkyl and ($C_2$-$C_{10}$)heterocyclyl, m and n are each independently 1-8, and fused rings A and B are each independently unsubstituted or substituted with at least one of J, ($C_1$-$C_{10}$)alkyl, ($C_2$-$C_{10}$)alkenyl, ($C_2$-$C_{10}$)alkynyl, ($C_1$-$C_{10}$)haloalkyl, ($C_1$-$C_{10}$)alkoxy, ($C_1$-$C_{10}$)haloalkoxy, ($C_1$-$C_{10}$)cycloalkyl($C_0$-$C_{10}$)alkyl, ($C_1$-$C_{10}$)heterocyclyl($C_0$-$C_{10}$)alkyl, ($C_1$-$C_{10}$)aryl($C_0$-$C_{10}$)alkyl, or ($C_1$-$C_{10}$)heteroaryl($C_0$-$C_{10}$)alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J. The variable J independently at each occurrence is selected from the group consisting of F, Cl, Br, I, OR, CN, $CF_3$, $OCF_3$, R, O, S, C(O), S(O), methylenedioxy, ethylenedioxy, $N(R)_2$, SR, S(O)R, $SO_2$R, $SO_2N(R)_2$, $SO_3$R, C(O)R, C(O)C(O)R, C(O)$CH_2$C(O)R, C(S)R, C(O)OR, OC(O)R, OC(O)OR, C(O)$N(R)_2$, OC(O)$N(R)_2$, C(S)$N(R)_2$, $(CH_2)_{0-2}$NHC(O)R, N(R)N(R)C(O)R, N(R)N(R)C(O)OR, N(R)N(R)C(O)$N(R)_2$, N(R)$SO_2$R, N(R)$SO_2N(R)_2$, N(R)C(O)OR, N(R)C(O)R, N(R)C(S)R, N(R)C(O)$N(R)_2$, N(R)C(S)$N(R)_2$, N(C(O)R)C(O)R, N(OR)R, C(=NH)$N(R)_2$, C(O)N(OR)R, and C(=NOR)R, wherein R is independently at each occurrence selected from the group consisting of hydrogen, ($C_1$-$C_{10}$)alkyl, ($C_1$-$C_{10}$)cycloalkyl, ($C_1$-$C_{10}$)cycloalkyl($C_1$-$C_{10}$)alkyl, ($C_1$-$C_{10}$)aryl, ($C_1$-$C_{10}$)aralkyl, ($C_1$-$C_{10}$)heterocyclyl, ($C_1$-$C_{10}$)heterocyclyl($C_1$-$C_{10}$)alkyl, ($C_1$-$C_{10}$)heteroaryl, and ($C_1$-$C_{10}$)heteroaryl($C_1$-$C_{10}$)alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

In various embodiments, the polyol can be derived at least in part from renewable (e.g., non-petroleum) sources. Advantageously, by deriving the polyol from renewable sources, the resulting polyisocyanate can be at least in part derived from renewable sources. For example, in some embodiments the polyol can be isosorbide:

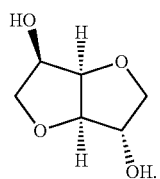

In some embodiments the polyol can be isomannide:

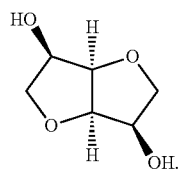

In some embodiments the polyol can be isoidide:

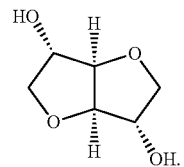

Isosorbide is a natural diol that can be derived from corn. Isosorbide, isomannide, and isoidide are three isomers of 1,4:3,6-dianhydrohexitol, and can be derived from, for example, D-glucose, D-mannose, and L-fructose, respectively. Isosorbide is the most widely available of the three isomers, as a by-product of the starch industry. Isosorbide, isomannide, and isoidide have characteristics including rigidity, thermal stability, chirality, and lack of toxicity, which makes these polyols highly desirable for use in synthesizing environmentally benign and useful polyisocyanates therefrom, and likewise the polyisocyanates are highly desirable for use in synthesizing environmentally benign and useful compounds such as polyurethanes.

The acid anhydride can have the structure:

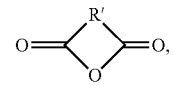

wherein R' corresponds to R' in Formula (I). Thus, R' can be selected from the group consisting of ($C_2$-$C_{10}$)alkanylene, ($C_2$-$C_{10}$)alkenylene, and ($C_2$-$C_{10}$)alkynylene. R' can be unsubstituted, or substituted with at least one J, as defined herein. In various embodiments, R' can be ethanylene (—$CH_2$—$CH_2$—), propanylene (—$CH_2$—$CH_2$—$CH_2$—), or butanylene (—$CH_2$—$CH_2$—$CH_2$—$CH_2$—). In some examples, the anhydride can be derived at least in part from renewable sources. Advantageously, by deriving the anhydride from renewable sources, the resulting polyisocyanate can be at least in part derived from renewable sources; if the polyol is also renewably derived, an even larger proportion of the polyisocyanate is renewably derived. In various embodiments, the anhydride can be succinic anhydride, which can be derived from succinic acid, which can be isolated from, for example, the products of sugar fermentation.

The contacting of the fused bicyclic polyol and the acid anhydride can be performed under any suitable conditions. In some examples, the anhydride can be used in excess, such as about 1.2 equivalents or less, about 1.4 equivalents, 1.6, 1.8, 2.0, 2.2, 2.4, 2.6, 2.8, or about 3.0 or more equivalents, with about 1 equivalent of bicyclic polyol. The reaction can be performed neat, or with any suitable solvent and using any suitable concentration. The reaction can be stirred or unstirred. The reaction can be cooled, unheated, heated, or any combination thereof. The reaction can be cooled such that the temperature of the reaction does not exceed about −20° C., or less, about −10° C., −5° C., 0° C., 5° C., 10° C., or about 20° C., or more. The reaction can be unheated. The reaction can be heated to any suitable temperature, for example, about 80° C., or less, about 90° C., 100, 110, 120, 130, 140, 150, 180, 200, 220, 240, 260, 280, or about 300° C. or higher. In some examples, substantially all of the reaction vessel can be heated, for example to avoid sublimation of the anhydride. The cooling, no heating, or heating can be performed for any suitable time, for example, about 10 min or less, about 30 min. 1 h, 2 h, 4 h, 6 h, 12 h, 18 h, 24 h, 1.5 d, 2 d, or about 3 d or more. The resulting polyacid can be carried forward to the next step crude or can be purified by any suitable technique. In some examples, the resulting crude polyacid is sufficiently pure such that little or no purification is required. In some embodiments, any solvent can be evaporated using standard techniques such as a rotating evaporator, and vacuum distillation or chromatography can be used to purify the polyacid.

The contacting of the fused bicyclic polyol and the acid anhydride provides a polyacid having the structure of Formula (I):

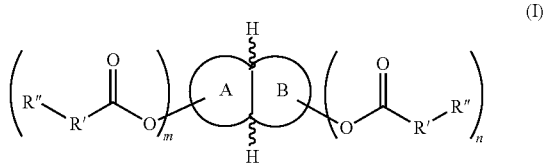

(I)

where Formula (I) is as described herein, wherein R" is —C(O)OH.

The method also can include contacting the polyacid and an acyl halide generator. The acyl halide generator can be any suitable acyl halide generator that reacts with a carboxylic acid to generate an acyl halide. For example, the acyl halide generator can be thionyl chloride, thionyl bromide, phosphorous pentachloride, phosphorus pentabromide, cyanuric fluoride, phosgene, diphosgene, triphosgene, oxalyl chloride, phosphorus tribromide, phosphorus trichloride, phosphoryl chloride, or any suitable combination thereof.

Contacting the polyacid and the acyl halide generator can be performed under any suitable conditions. In some examples, the acyl halide generator can be used in excess, such as about 1.2 equivalents or less, about 2 equivalents, 4, 6, 8, 10, 20, 50, 100, or about 500 or more equivalents, with about 1 equivalent of the polyacid. The reaction can be performed neat, or with any suitable solvent and at any suitable concentration. The reaction milieu can include catalytic quantities of dimethylformamide, such as about 0.001 equivalents or less, or about 0.01 equivalents, 0.01-0.1 equivalents, or about 0.1-0.5 equivalents or more. The reaction can be stirred or unstirred. The reaction can be cooled, unheated, heated, or any combination thereof. The reaction can be cooled to about −20° C., or less, about −10° C., 0° C., 10° C., or about 20° C., or more. The reaction can be unheated. The reaction can be heated to any suitable temperature, for example, about 30° C., or less, about 40, 50, 60, 70, or about 80° C. or higher. The cooling, no heating, or heating can be performed for any suitable time, for example, about 10 min or less, about 15 min, 20 min, 25 min. 30 min, 40 min, 50 min, 1 h, 2 h, 4 h, 6 h, 12 h, 18 h, 24 h, 1.5 d, 2 d, or about 3 d or more. The resulting polyacyl halide can be isolated in any suitable fashion, or can be carried through to the next step crude. In some embodiments, the crude polyacyl halide is sufficiently pure such that little or no purification is needed. For example, in some embodiments vacuum distillation or chromatography can be used to purify the polyacyl halide. In some embodiments, any solvent can be evaporated using standard techniques such as a rotating evaporator, and distillation can be used to remove the acyl halide generator from the acyl halide.

The contacting of the polyacid and the acyl halide generator provides a polyacyl halide having the structure of Formula (I) wherein R" is —C(O)X wherein X is halide. For example, the polyacyl halide can be a polyacyl chloride, or a diacyl chloride.

The method can include contacting the polyacyl halide and an azide generator. The azide generator can be any suitable azide generator that reacts with an acyl halide to generate an acyl azide, such as any suitable salt of an azide ion ($N_3^-$). For example, the azide generator can be sodium azide, trimethylsilyl azide, triethylsilyl azide, lithium azide, potassium azide, tetrabutylammonium azide, tert-butyldimethylsilyl azide, tert-butyldiphenylsilyl azide, or any suitable combination thereof. The contacting of the polyacid halide and an azide generator can provide a polyacyl azide having the structure of Formula (I) wherein R" is —C(O)$N_3$. The polyacyl azide can undergo a Curtius rearrangement to provide a polyisocyanate having the structure of Formula (I) wherein R" is —NCO; thus, the contacting of the polyacid halide and the azide generator under suitable conditions can provide a polyisocyanate having the structure of Formula (I) wherein R" is —NCO, such as a diisocyanate. The Curtius rearrangement can occur in a separate step from the contacting of the polyacid halide and the azide generator, or the Curtius rearrangement can occur in the same step.

Contacting the polyacyl halide and an azide generator can be performed under any suitable conditions. For example, in embodiments in which the polyacyl azide is generated and a discrete step is used to elicit the Curtius rearrangement and generate the polyisocyanate, the contacting of the polyacyl halide and the azide generator can occur in any suitable fashion. For example, the acyl azide generator can be used in excess, such as about 1.2 equivalents or less, about 2 equivalents, 3, 4, 5, 6, 7, 8, 10, 20, or about 30 or more equivalents, with about 1 equivalent of the polyacyl halide. The acyl azide generator can be used in an aqueous solution. The reaction can be performed neat, or with any suitable solvent, such as toluene, using any suitable concentration. The reaction can be stirred or unstirred. The reaction can be cooled, unheated, heated, or any combination thereof. The reaction can be cooled such that the temperature of the reaction does not exceed about −20° C., or less, about −10° C., −5° C., 0° C., 1° C., 2° C., 3° C., 4°, 5°, 10°, or about 20° C. or more. The reaction can be unheated. The reaction can be heated to any suitable temperature, for example, about 30° (or less, about 40° C., 60° C., 80° C., 100° C., or about 110° C., or higher. The cooling, no heating, or heating can be performed for any suitable time, for example, about 10 min or less, or about 15 min, 20 min, 25 min. 30 min, 40 min, 50 min, 1 h, 2 h, 4 h, 6 h, 12 h, 18 h, 24 h, 1.5 d, 2 d, or about 3 d or more. The resulting azide can be worked up in any suitable fashion, for example by removing any aqueous phase, recovering any organic material from the aqueous phase, washing the organic phase with at least one of aqueous base, water, and brine, and drying the organic phase. In various embodiments, the resulting azide is not isolated any further than as a worked up organic solution, due at least in part to the explosion risk of organic azides in a concentrated state.

In embodiments in which the polyacyl azide is generated and a discrete step is used to elicit the Curtius rearrangement and generate the polyisocyanate, the polyacyl azide can be treated in any suitable fashion to generate the polyisocyanate. In various embodiments, the polyacyl azide can be added neat or as a solution, for example as a solution in toluene, to a solvent, such as refluxing toluene. The polyacyl azide can be added to the solvent at any rate, for example at or less than a rate sufficient to approximately maintain steady refluxing of the solvent and steady release of nitrogen gas but not so fast as to generate nitrogen at a rate that is uncontrolled and not so fast as to cause uncontrolled boiling of the solvent. The reaction can be stirred or unstirred. Prior to and during addition of the polyacyl azide to the solvent, the reaction can be heated or maintained at any suitable temperature, for example, about 30° C. or less, about 40, 60, 80, 100, or about 110° 2 or higher. Once the addition of the polyacyl azide is complete, the reaction can be complete, or the reaction can be allowed to continue for any suitable amount of time. In some embodiments, once the addition of the polyacyl azide is complete, the reaction is heated or maintained at any suitable temperature, such as about reflux temperature, for any suitable amount of time, for example, about 5 min or less, or about 10 min, about 15 min, 20 min, 25 min, 30 min, 40 min, 50 min, 1 h, 2 h, 4 h, 6 h, 12 h, 18 h, 24 h, 1.5 d, 2 d, or about 3 d or more. The resulting polyisocyanate can be purified in any suitable fashion. In some embodiments, the crude polyisocyanate is sufficiently pure such that little or no purification is needed. In some examples, any solvent can be evaporated using standard techniques such as a rotating evaporator, and the polyisocyanate can be purified using vacuum distillation or chromatography.

In examples in which the polyacyl azide is generated but the polyisocyanate is generated in a single step, contacting the polyacyl halide and the azide generator can occur in any suitable fashion. In some examples, the azide generator can be used in excess, such as about 1.2 equivalents or less, about 2 equivalents, 4, 6, 8, 10, 20, or about 30 or more equivalents, with about 1 equivalent of the polyacyl halide. The reaction can be performed neat, or with any suitable solvent. In some examples, the azide generator can be added neat or in a solution having a suitable concentration to the polyacyl halide. The addition can be performed at a rate sufficient that the nitrogen gas evolution that occurs is controlled, and such that the temperature is maintained at or below about 50° C., or about 60° C., 70° C., 80° C., 90° C., 100° C., 110° C., 120° C., 130° C., 140° C., 150° C., 160° C., 170° C., or about 180° C., or above. In various embodiments, the reaction milieu can include suitable concentrations of a phase transfer catalyst, such as a tetra($C_{1-10}$) alkylammonium halide salt (e.g. when using sodium azide as the azide generator), alkaloid-derived phase transfer catalysts, or phosphonium salts; in other embodiments, no phase transfer catalyst is present. In some embodiments, In some embodiments, a silicon-based reagent can be used such as trimethylsilyl chloride, trimethylsilyl triflate, or tri($C_{1-20}$alkyl)silyl halide, or the analogous germanium- or tin-based reagent can be used (e.g. tetra($C_{1-20}$ alkyl)germanium halide or tri($C_{1-20}$ alkyl)germanium halide)); in other embodiments, no silicon-based, germanium-based, or tin-based reagent is used. Once the addition is complete, the reaction can be maintained at the temperature used during the addition of the azide generator or at a different temperature for any suitable duration, for example, about 10 min or less, or about 15 min, 20 min, 25 min, 30 min, 40 min, 50 min, 1 h, 2 h, 4 h, 6 h, 12 h, 18 h, 24 h, 1.5 d, 2 d, or about 3 d or more. The resulting polyisocyanate can be purified in any suitable fashion. In some embodiments, the crude polyisocyanate is sufficiently pure such that little or no purification is needed. In some examples, any solvent can be evaporated using standard techniques such as a rotating evaporator, and the polyisocyanate can be purified using vacuum distillation or chromatography.

In some examples, the polyacid is contacted with suitable reagents under suitable conditions to undergo a Schmidt reaction to directly yield the polyacyl azide or polyisocyanate. Reagents and conditions suitable for elicitation of a Schmidt reaction are readily known to one of ordinary skill in the art, for example hydroazoic acid can be contacted with the polyacid with expulsion of nitrogen to give the polyisocyanate.

Polyurethane.

In various embodiments, the present invention provides a polyurethane derived from any suitable compound of Formula (I). In some examples, a compound having the structure of Formula (I) where R"=—NCO can be synthesized from any of the compounds of Formula (I) having R"=—C(O)OH, —C(O)O⁻X⁺, —C(O)F, —C(O)Cl, —C(O)Br, —C(O)I, —C(O)N₃ by using an embodiment of the method of the present invention or by using another method. The compound of Formula (I) with R"=—NCO, either made using the polyacid, polyacid salt, polyacyl halide, or polyacyl azide, or synthesized via a different route, can be combined with any one or more suitable alcohols to cause a polymerization reaction between the hydroxyl moieties of the alcohol and the isocyanate moieties of the polyisocyanate to create a polyurethane. The polyurethanes of the present invention include any polyurethane that is a reaction product of at least a compound of Formula (I) having R"=—NCO and an alcohol, such as a polyol, chain extender, and the like. Thus, the polyurethanes of the present invention include a plurality of subunits having the structure of Formula (II):

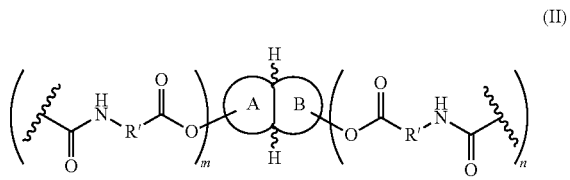

For a polyurethane to include a plurality of subunits having the structure of Formula (II), the structure of Formula (II) occurs at least twice in the polyurethane molecule. The polyurethane including a plurality of subunits of Formula (II) can be derived from a suitable compound of Formula (I); therefore, various aspects of Formula (II) have the equivalent features as described herein for Formula (I). However, the polyurethane including Formula (II) can be derived from any suitable compound, and the method of derivation is not restricted to compounds of Formula (I).

Formula (II) includes fused rings A and B, which share a single carbon-carbon bond. Rings A and B can be the same or different, and are each independently selected from ($C_5$-$C_{10}$)cycloalkyl and ($C_2$-$C_{10}$)heterocyclyl, wherein the designated number of carbon atoms includes the two carbon atoms that are shared by rings A and B. In some examples, rings A and B can be the same size, and can both be cyclopentyl, cyclohexyl, cyclopentyl, cyclooctyl, cyclononyl, or cyclodecyl. The hydrogen atom attached to each shared carbon atom can have any suitable stereochemical configuration with respect to each other and with respect to other functional groups on rings A and B, and can be syn or anti.

Rings A and B can have any suitable number and variety of functional groups thereon. Rings A and B each include one or more ester substituents having the formula —C(O)—NH—R'—C(O)O—. The one or more ester substitutents have an ester moiety at the point of attachment to fused rings A and B, and can have a carbamate moiety at the other end that can be formed from the reaction of an —OH group of the one or more alcohols used to synthesize the polyurethane and an —NCO group of the polyisocyanate of Formula (I) wherein R" is —NCO. The variables m and n are each independently 1-8; thus, Rings A and B can each independently have about 1 to 8 ester substituents thereon. The variables m and n can have different values, or the variable m and n can be equal. The variables m and n can each be 1. Rings A and B can each have the same type and number of ester substituents or a different type and number of ester substituents. Rings A and B each have at least one ester substituent. In some examples, fused rings A and B can be each independently unsubstituted with the exception of the ester substituents.

In some examples, fused rings A and B can be each independently substituted with at least one of J, $(C_1-C_{10})$ alkyl, $(C_2-C_{10})$alkenyl, $(C_2-C_{10})$alkynyl. $(C_1-C_{10})$haloalkyl, $(C_1-C_{10})$alkoxy. $(C_1-C_{10})$haloalkoxy, $(C_1-C_{10})$cycloalkyl $(C_0-C_{10})$alkyl, $(C_1-C_{10})$heterocyclyl$(C_0-C_{10})$alkyl, $(C_1-C_0)$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J. The variable J independently at each occurrence is selected from the group consisting of F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-2}$NHC(O)R, N(R)N(R)C(O)R, N(R)N(R)C(O)OR, N(R)N(R)C(O)N(R)_2, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(C(O)R)C(O)R, N(OR)R, $C(=NH)N(R)_2$, C(O)N(OR)R, and C(=NOR)R, wherein R is independently at each occurrence selected from the group consisting of hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl. $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

In Formula (II), the variable R' in the ester substituent is selected from the group consisting of $(C_2-C_{10})$alkanylene, $(C_2-C_{10})$alkenylene, and $(C_2-C_{10})$alkynylene. In some examples, R' can be unsubstituted, and in other examples, R' can be substituted with at least one J, as defined herein. In various examples, R' can be ethanylene (—$CH_2$—$CH_2$—), propanylene (—$CH_2$—$CH_2$—$CH_2$—), or butanylene (—$CH_2$—$CH_2$—$CH_2$—$CH_2$—).

In some embodiments, at least one of the ester substituents having the formula —C(O)—NH—R'—C(O)O— is alpha to a carbon atom shared by rings A and B, for example, the ester substituent can be substituted on an atom of ring A or B that is bound to a carbon atom shared by rings A and B. In some examples, at least one of the one or more ester substituents on each of rings A and B is alpha to a carbon atom shared by rings A and B. In some examples, at least one of the one or more ester substituents on ring A is alpha to a carbon atom shared by rings A and B, and at least one of the ester substituents on ring B is alpha to the other carbon atom shared by rings A and B, and m can equal n or both m and n can be 1.

In some examples, at least one of rings A and B include at least one oxygen atom. In some embodiments, each of rings A and B include at least one oxygen atom. In some examples, each of rings A and B is a tetrahydrofuran ring (e.g. cyclotetramethylene oxide, having any suitable substituents), where each of the two carbon atoms shared by rings A and B is alpha to the oxygen atom in at least one of rings A and B. In some examples, each of rings A and B is a tetrahydrofuran ring, where one the two carbon atoms shared by rings A and B is alpha to the oxygen atom in ring A, and the other carbon atom shared by rings A and B is alpha to the oxygen atom in ring B.

In some embodiments, m and n are 1, and each of rings A and B includes at least one oxygen atom, such that one the two carbon atoms shared by rings A and B is alpha to the at least one oxygen atom in ring A and alpha to the ester substituent on ring B, and the other carbon atom shared by rings A and B is alpha to the at least one oxygen atom in ring B and alpha to the ester substituent on ring A.

In various embodiments, the subunit having the structure of Formula (II) can be:

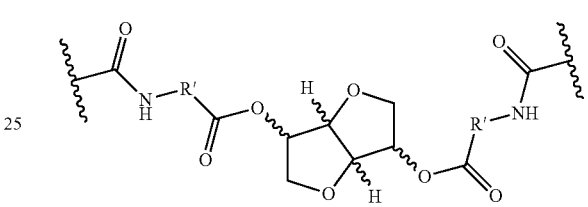

In some examples, a polyurethane including a plurality of this subunit can be derived from diisocyanates provided by various embodiments of the present invention, which in turn can be derived from suitable fused bicyclic diols and a suitable cyclic anhydride using various methods of the present invention.

In various embodiments, the subunit having the structure of Formula (II) can be:

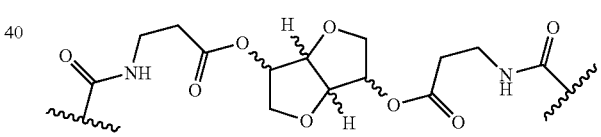

In some examples, a polyurethane including a plurality of this subunit can be derived from diisocyanates provided by various embodiments of the present invention, which in turn can be derived from suitable fused bicyclic diols and succinic anhydride using various methods of the present invention.

In various embodiments, the subunit having the structure of Formula (II) has a fused bicyclic tetrahydrofuran ring system with the stereochemistry of an isosorbide ring system, having the structure:

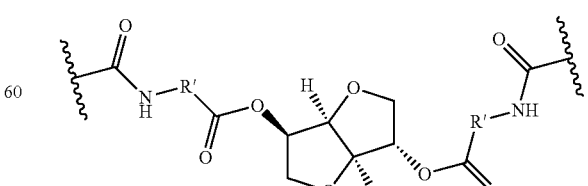

In some examples, a polyurethane including a plurality of this subunit can be derived from diisocyanates provided by various embodiments of the present invention, which in turn can be derived from isosorbide and a suitable anhydride using various methods of the present invention.

In various embodiments, the compound of Formula (II) is a diisocyanate having a fused bicyclic tetrahydrofuran ring system with the stereochemistry of an isosorbide ring system, where R' is ethanylene, having the structure:

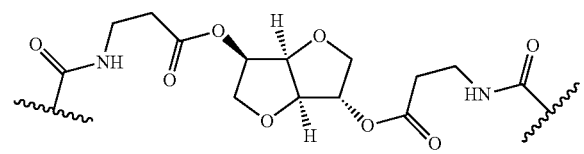

In some examples, a polyurethane including a plurality of this subunit can be derived from diisocyanates provided by various embodiments of the present invention, which in turn can be derived from isosorbide and succinic anhydride using various methods of the present invention.

In various embodiments, the compound of Formula (II) is a diisocyanate having a fused bicyclic tetrahydrofuran ring system with the stereochemistry of an isomannide ring system, having the structure:

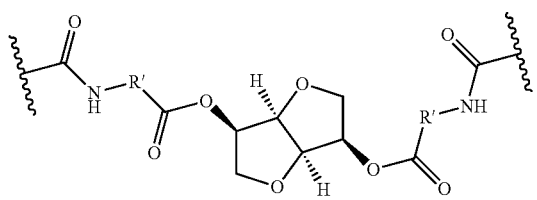

In some examples, a polyurethane including a plurality of this subunit can be derived from diisocyanates provided by various embodiments of the present invention, which in turn can be derived from isomannide and a suitable cyclic anhydride using various methods of the present invention.

In various embodiments, the compound of Formula (II) is a diisocyanate having a fused bicyclic tetrahydrofuran ring system with the stereochemistry of an isomannide ring system, where R' is ethanylene, having the structure:

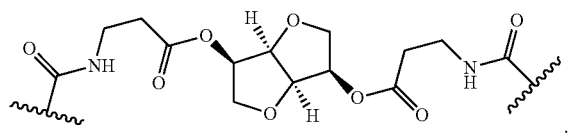 [SMILES: *C(=O)NCCC(=O)O[C@@H]1CO[C@H]2[C@@H]1OC[C@H]2OC(=O)CCNC(*)=O]

In some examples, a polyurethane including a plurality of this subunit can be derived from diisocyanates provided by various embodiments of the present invention, which in turn can be derived from isomannide and succinic anhydride using various methods of the present invention.

In various embodiments, the compound of Formula (II) is a diisocyanate having a fused bicyclic tetrahydrofuran ring system with the stereochemistry of an isoidide ring system, having the structure:

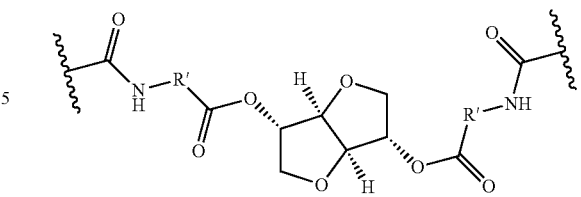

In some examples, a polyurethane including a plurality of this subunit can be derived from diisocyanates provided by various embodiments of the present invention, which in turn can be derived from isoidide and a suitable cyclic anhydride using various methods of the present invention.

In various embodiments, the compound of Formula (II) is a diisocyanate having a fused bicyclic tetrahydrofuran ring system with the stereochemistry of an isoidide ring system, where R' is ethanylene, having the structure:

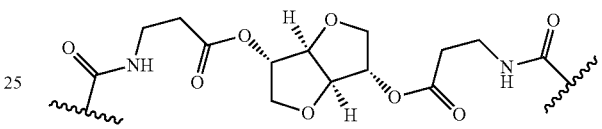

In some examples, a polyurethane including a plurality of this subunit can be derived from diisocyanates provided by various embodiments of the present invention, which in turn can be derived from isoidide and succinic anhydride using various methods of the present invention.

Alcohols that can be contacted with polyisocyanates to generate the polyurethanes of the present invention include any suitable alcohol. In one example, the alcohol is a polyol. In some examples, the polyol can be isosorbide, isomannide, isoidide, or any combination thereof. Advantageously, by using a polyol that is renewably derived in combination with a polyisocyanate that is at least in part renewably derived, the resulting polyurethane can be derived in greater proportion from renewable materials. For example, the polyol can be one polyol, or a mixture of different polyols. In some examples, the polyol can be sorbitol or glycerine. The polyol can be a polyester polyol, a polyether polyol, or any combination thereof. Polyether polyols can include any poly($C_{1-10}$ hydrocarbylene oxide), wherein the hydrocarbylene group can include any alkylene, alkenylene, alkynylene, arylene, or cycloalkylene group, wherein the hydrocarbylene can optionally be substituted with any suitable organic group, halide, or hydroxyl group. Examples of polyethers can include polyethylene glycol, polypropylene glycol, polybutylene glycol, dipropylene glycol, diethylene glycol, or sucrose. For example, polyether polyols can include any polyether polyol derived from esterification of a ($C_{2-20}$)diacid and a glycol or polyol, or any polyether polyol derived from transesterification of poly(ethyleneterephthalate) or dimethylterepthalate with a glycol or polyol.

In addition to the polyisocyanate and the alcohol, the polyurethanes of the present invention can derived from mixtures that include any other suitable ingredient, such as, for example, chain extenders, cross linkers, catalysts, surfactants, other isocyanates, stabilizers, lubricants, dyes, pigments, inorganic and/or organic fillers, and reinforcing materials such as impact modifiers.

The chain extender, if present, can be any suitable chain extender. For example, the chain extender can be 1,4-butanediol, 1,6-hexanediol, 1,8-octandiol, 1,9-nonanediol, 1,10-decanediol, 1,12-dodecanediol, 1,4-cyclohexanedimethanol, p-xylene glycol, and 1,4-bis(2-hydroxyethoxy)benzene.

Other polyisocyanates can include any suitable polyisocyanate. For example, the other polyisocyanate can be 4,4'-methylenediphenyl diisocyanate (MDI), methylene bis(cyclohexyl)diisocyanate (H12MDI), p-phenylene diisocyanate (p-PDI), trans-cyclohexane-1,4-diisocyanate (CHDI) or a mixture of the cis and trans isomers, 1,6-hexamethylene diisocyanate (DICH), 2,4-toluene diisocyanate (2,4-TDI), p-tetramethylxylene diisocyanate (p-TMXDI), m-tetramethylxylene diisocyanate (m-TMXDI), isomers thereof, and combinations thereof.

The polyurethanes of the present invention are easily adaptable to a variety of fabrication techniques including solvent casting, blow molding, machining to various shapes and other conventional processing techniques such as injection molding and extrusion.

The polyurethanes of the present invention can have any suitable range of molecular weight. For example, the polyurethane can have a molecular weight of about 5000 to about 1,000,000, or about 2500 to 10,000,000.

The present invention provides any solution or dispersion of a polyurethane of the present invention. Such a dispersion can include an aqueous liquid having any suitable proportion of polyurethane therein. The dispersion can include about 50% water or less, about 60% water, 70%, 80%, 85%, 90%, 91%, 92%, 93%, 94%, 95%, 96%, 97%, 98%, 99%, 99.9%, or 99.99% water, or more, by mass. The dispersion can include about 50% of the polyurethane or more, or about 40% polyurethane, 30%, 20%, 15%, 10%, 9%, 8%, 7%, 6%, 5%, 4%, 3%, 2%, 1%, 0.1%, 0.01%, 0.001%, 0.0001%, or about 0.00001% or less polyurethane by mass. The aqueous dispersion can include any other suitable component, or substantially no other component other than water and polyurethane.

Embodiments of the present invention encompass any suitable method of generating polyurethanes from the compounds of Formula (I), for example by contacting a compound of Formula (I) having R"=—NCO with any suitable alcohol under conditions sufficient to generate a polyurethane. The conditions can be any suitable conditions. The reaction can be neat or can include a solvent with any suitable concentration of reactants. The reaction can include a catalyst, or the reaction can include no catalyst. In addition to the polyisocyanate and the alcohol, the reaction can include any other suitable ingredient, such as, for example, chain extenders, cross linkers, catalysts, surfactants, or other isocyanates. The reaction can be cooled, not heated, heated, or any combination thereof. The reaction can be cooled such that the temperature of the reaction does not exceed about −20° C., or less, about −10° C., −5° C., 0° C., 5° C., 10° C., or about 20° C., or more. The reaction can be unheated. The reaction can be heated to any suitable temperature, for example, about 80° C., or less, about 90° C., 100, 110, 120, 130, 140, 150, 180, 200, 220, 240, 260, 280, or about 300° C., or higher. The cooling, no heating, or heating can be performed for any suitable time, for example, about 10 min or less, about 30 min, 1 h, 2 h, 4 h, 6 h, 12 h, 18 h, 24 h, 1.5 d, 2 d, or about 3 d or more. Any suitable work up or purification procedure can be used. In some examples, the crude polyurethane is sufficiently pure such that additional purification is not needed.

EXAMPLES

The present invention can be better understood by reference to the following examples which are offered by way of illustration. The present invention is not limited to the examples given herein.

General. All reactions were performed with magnetic stirring. All non-aqueous reactions were performed under an argon atmosphere. HPLC-grade toluene and reagents of the most economical grade were used as received. Reactions were monitored by $^1$H NMR spectroscopy on Bruker DRX-400 or DRX-600 instruments. NMR spectra were calibrated using residual undeuterated solvent as an internal reference. $^1$H NMR multiplicities refer to apparent multiplicities as determined visually: s=singlet, d=doublet, t=triplet, q=quartet, m=multiplet, b=broad. Thin-layer chromatography was carried out on Grace Davison Davisil silica gel plates (0.25 mm thickness, with fluorescent indicator). Isosorbide-Based Diisocyanate.

Example 1. Synthesis of Diacid 3

As illustrated in Scheme 2, diacid 3 was synthesized from isosorbide 1 and succinic anhydride 2.

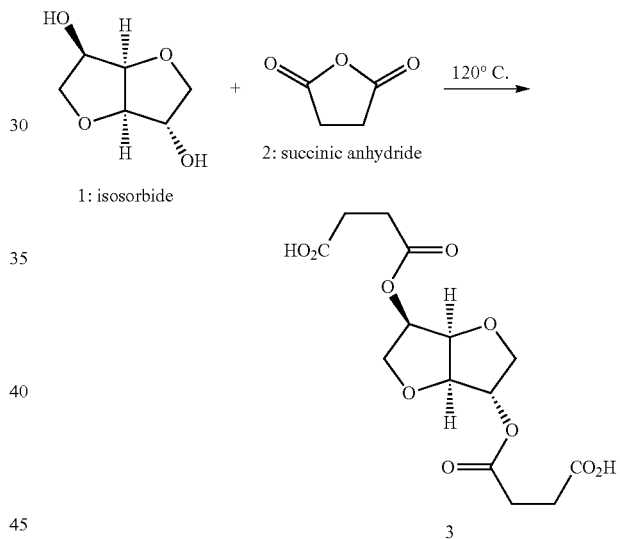

A mixture of isosorbide (1, 7.31 g, 50 mmol) and succinic anhydride (2, 11.51 g, 115 mmol, 2.3 equiv) was heated at 120° C. for 24 hr to give diacid 3 as a viscous orange oil. To avoid sublimation of succinic anhydride 2, the entire reaction vessel was heated. The chemical yield was estimated by $^1$H NMR analysis to be approximately 100%. Sublimation of succinic anhydride (2) from the crude material afforded a sample of diacid 3 for analysis. 3: $R_f$=0.43 (silica gel. EtOAc); $[\alpha]_D^{23}$=+90.9° (c=1.00, CHCl$_3$); IR (thin film): $\nu_{max}$=1739, 1716 cm$^{-1}$; $^1$H NMR (400 MHz, CDCl$_3$): δ=10.51 (br, 2H), 5.21 (s, 1H), 5.17 (q, J=5.4 Hz, 1H), 4.83 (t, J=5.1 Hz, 1H), 4.47 (d, J=4.7, 1H), 3.94 (m, 3H), 3.81 (dd, J=10.0, 5.1 Hz, 1H), 2.69 (s, 4H), 2.65 (m, 4H); $^{13}$C NMR (100 MHz, CDCl$_3$): δ=178.01, 177.95, 171.71, 171.33, 85.88, 80.87, 78.37, 74.42, 73.33, 70.54, 29.04, 29.01, 28.98, 28.76 ppm; HRMS (ESI-QTOF) calcd for C$_{14}$H$_{17}$O$_{10}$$^+$ [M−H$^+$]: 345.0822, found: 345.0827.

Example 2. Synthesis of Diacid Chloride 4

As illustrated in Scheme 3, diacid chloride 4 was synthesized from diacid 3.

Scheme 3. Synthesis of diacid chloride 4.

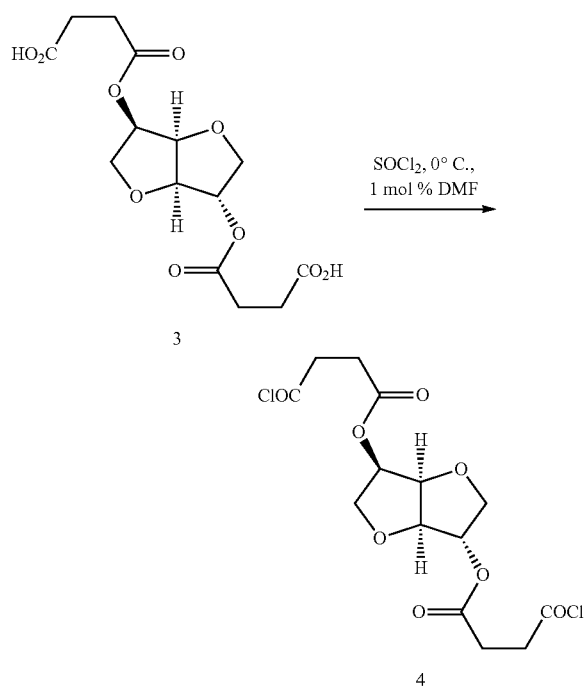

To a solution of crude diacid 3 (50 mmol) in thionyl chloride (100 mL) at 0° C. was added dimethylformamide (0.05 mL, 0.5 mmol, 0.01 equiv). Vigorous gas evolution was observed for approximately 30 min. After another 1.5 hr. excess thionyl chloride was distilled out under reduced pressure (30° C.) to give diacid chloride 4 as an orange oil. The chemical yield was estimated by $^1$H NMR analysis to be approximately 85%. A sample of diacid chloride 4 for analysis was obtained by the reaction of a purified sample of diacid 3. 4: $R_f$=0.35 (silica gel, EtOAc); $[\alpha]_D^{23}$=+49.0° (C=1.00, CHCl$_3$); IR (thin film) $\nu_{max}$=1794, 1747 cm$^{-1}$; $^1$H NMR (400 MHz, CDCl$_3$): δ=5.23 (d, J=3.1 Hz, 1H), 5.18 (q, J=5.4 Hz, 1H), 4.84 (t, J=5.1 Hz, 1H), 4.47 (d, J=4.7 Hz, 1H), 3.94 (m, 3H), 3.83 (dd, J=10.1, 4.9 Hz, 1H), 3.23 (m, 4H), 2.74 (td, J=6.6, 2.9 Hz, 2H), 2.69 (t, J=6.4 Hz, 2H); $^{13}$C NMR (100 MHz, CDCl$_3$): δ=173.11, 173.02, 170.45, 170.15, 85.89, 80.83, 78.68, 74.70, 73.28, 70.58, 41.76, 41.68, 29.40, 29.14 ppm.

Example 3. Synthesis of Diacyl Azide 5

As illustrated in Scheme 4, diacyl azide 5 was synthesized from diacid chloride 4.

Scheme 4. Synthesis of diacyl azide 5.

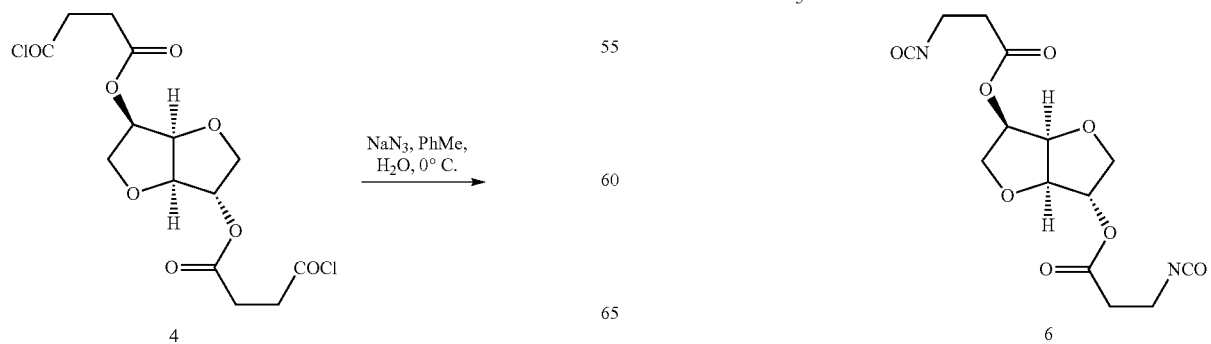

A solution of crude diacid chloride 4 (50 mmol) in toluene (125 mL) was added dropwise over the course of 40 min to an aqueous solution of sodium azide (16.25 g, 250 mmol, 5 equiv) at 0° C. The rate of addition was controlled so that the internal temperature of the reaction did not exceed 3 OC. The reaction was continued at 0° C. for 20 min after complete addition. The reaction mixture was partitioned into two phases, and the organic phase was washed with 1×100 mL 10% potassium carbonate solution, 1×100 mL water, and 2×100 mL brine, then dried over Na$_2$SO$_4$. Diacyl azide 5 was not concentrated due to its instability in pure form. The chemical yield of diacyl azide 5 from isosorbide (1) was estimated by $^1$H NMR analysis of the crude material using EtOAc as an internal standard to be approximately 85%. 5: $R_f$=0.60 (silica gel, EtOAc); IR (PhMe) $\nu_{max}$=2138, 1746, 1721 cm$^{-1}$; $^1$H NMR (400 MHz, CDCl$_3$ containing <5% PhMe and <1% EtOAc): δ=5.70 (d, J=3.3 Hz, 1H), 5.52 (q, J=5.3 Hz, 1H), 5.22 (t, J=5.1 Hz, 1H), 4.86 (d, J=4.7 Hz, 1H), 4.42 (m, 2H), 4.24 (d, J=5.3 Hz, 2H), 3.08-2.90 (m, 8H).

Example 4. Synthesis of Diisocyanate 6

As illustrated in Scheme 5, diisocyanate 6 was synthesized from diacyl azide 5.

Scheme 5. Synthesis of diisocyanate 6.

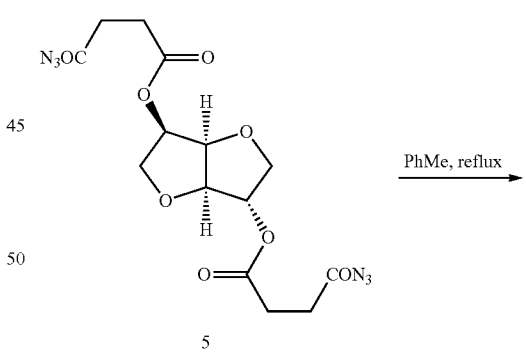

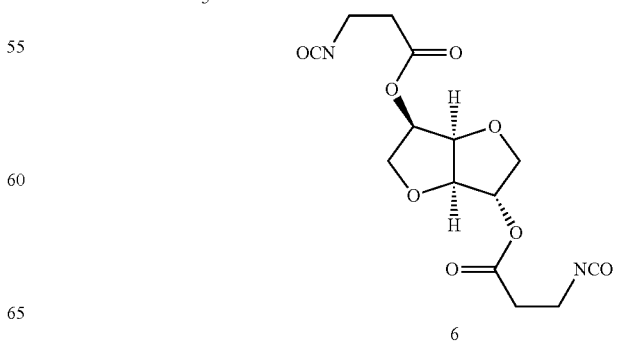

A toluene solution of diacyl azide 5 (50 mmol, toluene recovered from Example 3) was added dropwise over the course of 45 min to 10 mL of toluene at 110° C. The rate of addition was controlled so that a steady reflux rate and steady gas formation were achieved. The reaction was continued for 15 min after complete addition. Concentration under reduced pressure gave crude diisocyanate 6 as a dark orange oil. Diisocyanate 6 was purified by distillation (186-189° C., 54 mTorr) to give a light orange oil [10.19 g, 60% overall yield from isosorbide (1)]. 6: $R_f$=0.70 (silica gel, EtOAc); $[\alpha]_D^{23}$=+69.0° (c=1.00, CHCl$_3$); IR (thin film) $\nu_{max}$=2274, 1747 cm$^{-1}$; $^1$H NMR (600 MHz, CDCl$_3$): δ=5.26 (d, J=3.1 Hz, 1H), 5.21 (q, J=5.5 Hz, 1H), 4.87 (t, J=5.1 Hz, 1H), 4.50 (d, J=4.7 Hz, 1H), 3.97 (m, 3H), 3.85 (dd, J=10.1, 5.0 Hz, 1H), 3.60 (m, 4H), 2.67 (t, J=6.4 Hz, 2H), 2.62 (t, J=6.4 Hz, 2H); $^{13}$C NMR (150 MHz. CDCl$_3$): δ=170.18, 169.90, 123.40, 123.30, 85.97, 80.81, 78.54, 74.57, 73.35, 70.55, 38.67, 38.65, 35.69, 35.46 ppm; HRMS (ESI-QTOF) calcd for $C_{14}H_{17}N_2O_8^+$ [M+H]: 341.0985, found: 341.0979.

Example 5. Synthesis of Diisocyanate 6

As illustrated in Scheme 6, diisocyanate 6 was synthesized from diacid chloride 4.

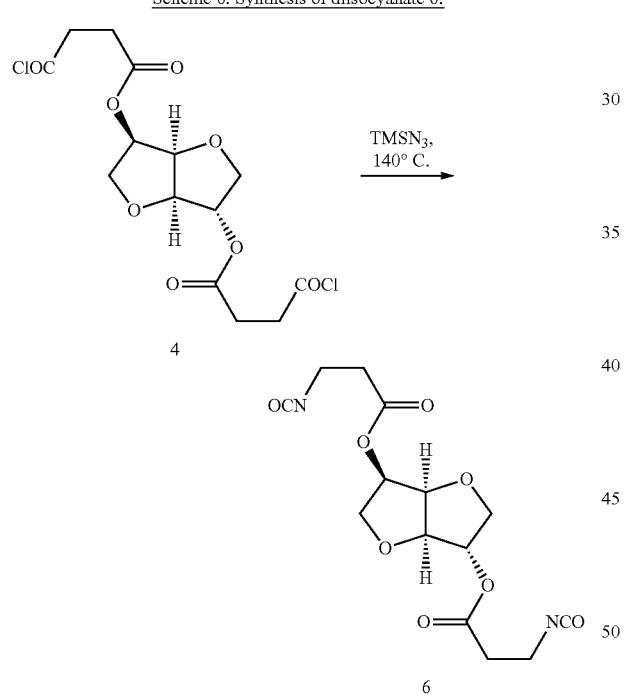

Trimethylsilyl azide (4.0 mL, 30 mmol, 6 equiv) was added dropwise to diacid chloride 4 (1.92 g, 5 mmol) at 140° C. resulting in vigorous gas evolution. The reaction was continued at 140° C. for 30 min after complete addition. Concentration under reduced pressure gave crude diisocyanate 6 as a dark red oil. The chemical yield of diisocyanate 6 from isosorbide (1) was estimated by $^1$H NMR analysis to be approximately 50%.
Isomannide-Derived Diisocyanate.

Example 6. Synthesis of Diacid 8

As illustrated in Scheme 7, diacid 8 was synthesized from isomannide 7 and succinic anhydride 2.

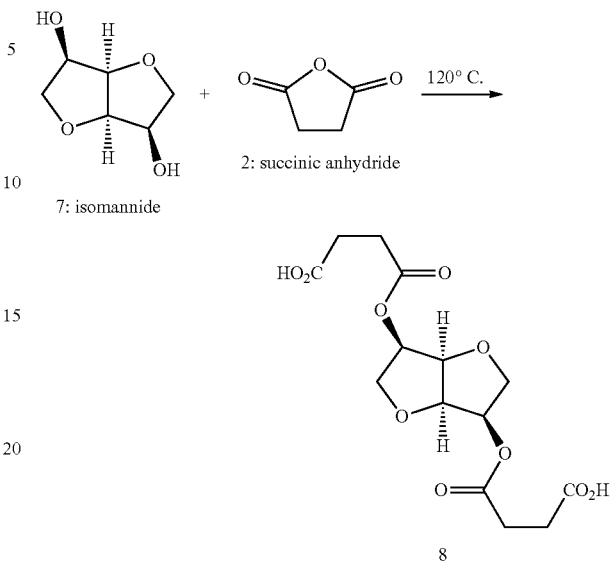

A mixture of isomannide (7, 7.31 g, 50 mmol, 1 equiv) and succinic anhydride (2, 11.51 g, 115 mmol, 2.3 equiv) was heated at 120° C. for 24 hr to give diacid 8 as a viscous orange oil. To avoid sublimation of succinic anhydride 2, the entire reaction vessel was heated. Vacuum sublimation of succinic anhydride (2) from the crude material affords a sample of diacid 8 for analysis. 8: $R_f$=0.38 (silica gel, EtOAc); $[\alpha]_D^{23}$=+116.9 (c=1.00, CHCl$_3$); IR (thin film): $\nu_{max}$=1741, 1717 cm$^{-1}$; $^1$H NMR (400 MHz, CDCl$_3$): δ=8.29 (br, 2H), 5.10 (d, J=5.8 Hz, 2H), 4.68 (dd, J=9.3, 3.8 Hz, 2H), 4.01 (dd, J=9.6, 6.1 Hz, 2H), 3.79 (dd, J=9.6, 6.3 Hz, 2H), 2.77-2.70 (m, 4H), 2.70-2.65 (m, 4H) ppm; $^{13}$C NMR (100 MHz, CDCl$_3$): δ=178.20, 171.37, 80.58, 73.98, 70.72, 29.40, 29.25 ppm; HRMS (ESI-QTOF) calcd for $C_{14}H_{17}O_{10}^-$ [M−H$^+$]: 345.0822, found: 345.0821; DSC (He, 10° C. min$^{-1}$): $T_g$=−2° C.

Example 7. Synthesis of Diacid Chloride 9

As illustrated in Scheme 8, diacid chloride 9 was synthesized from diacid

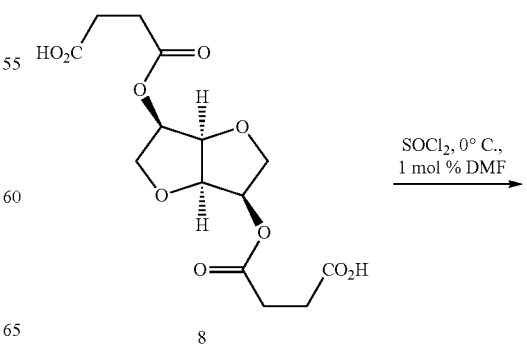

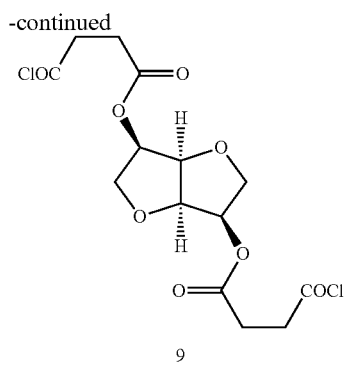

9

To a solution of crude diacid 8 (1 equiv) in thionyl chloride at 0° C. was added dimethylformamide (0.01 equiv). Vigorous gas evolution was observed for approximately 30 min. After another 1.5 hr, excess thionyl chloride was distilled out under reduced pressure (30° C.) to give diacid chloride 9. The chemical yield was estimated by $^1$H NMR analysis. A sample of diacid chloride 9 for analysis was obtained by the reaction of a purified sample of diacid 8. 9: $^1$H NMR (400 MHz, CDCl$_3$): δ=5.13-5.06 (m, 2H), 4.70-4.65 (m, 2H), 4.03 (dd, J=9.4, 6.3 Hz, 2H), 3.80 (dd, J=9.4, 6.6 Hz, 2H), 3.23 (td, J=6.5, 4.0 Hz, 4H), 2.78-2.72 (m, 4H) ppm; $^{13}$C NMR (100 MHz, CDCl$_3$): δ=178.20, 171.37, 80.58, 73.98, 70.72, 29.40, 29.25 ppm.

Example 8. Synthesis of Diacyl Azide 10

As illustrated in Scheme 9, diacyl azide 10 was synthesized from diacid chloride 9.

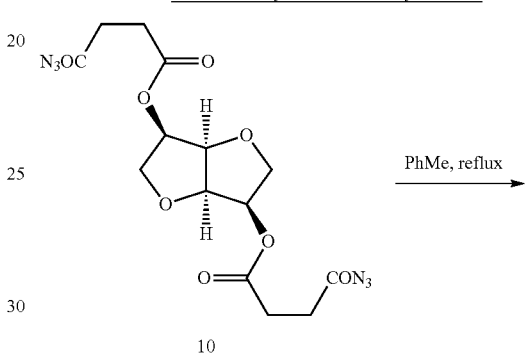

A solution of crude diacid chloride 9 (50 mmol, 1 equiv) in toluene was added dropwise to an aqueous solution of sodium azide (16.25 g, 250 mmol, 5 equiv) at 0° C. The rate of addition was controlled so that the internal temperature of the reaction did not exceed 3° C. The reaction was continued at 0° C. for 20 min after complete addition. The reaction mixture was partitioned into two phases, and the organic phase was washed once with 100 mL 10% potassium carbonate solution, once with 100 mL water, and twice with 100 mL brine, then dried over Na$_2$SO$_4$. Diacyl azide 10 was not concentrated due to its instability in pure form. The chemical yield of diacyl azide 10 from isomannide (7) was estimated by $^1$H NMR analysis of the crude material. 10: $^1$H NMR (400 MHz, CDCl$_3$): δ=5.32-5.23 (m, 2H), 4.88-4.81 (m, 2H), 4.21 (dd, J=9.5, 6.5 Hz, 2H), 4.01 (dd, J=9.5, 6.7 Hz, 2H), 2.94-2.79 (m, 8H) ppm.

Example 9. Synthesis of Diisocyanate 11

As illustrated in Scheme 10, diisocyanate 11 was synthesized from diacyl azide 10.

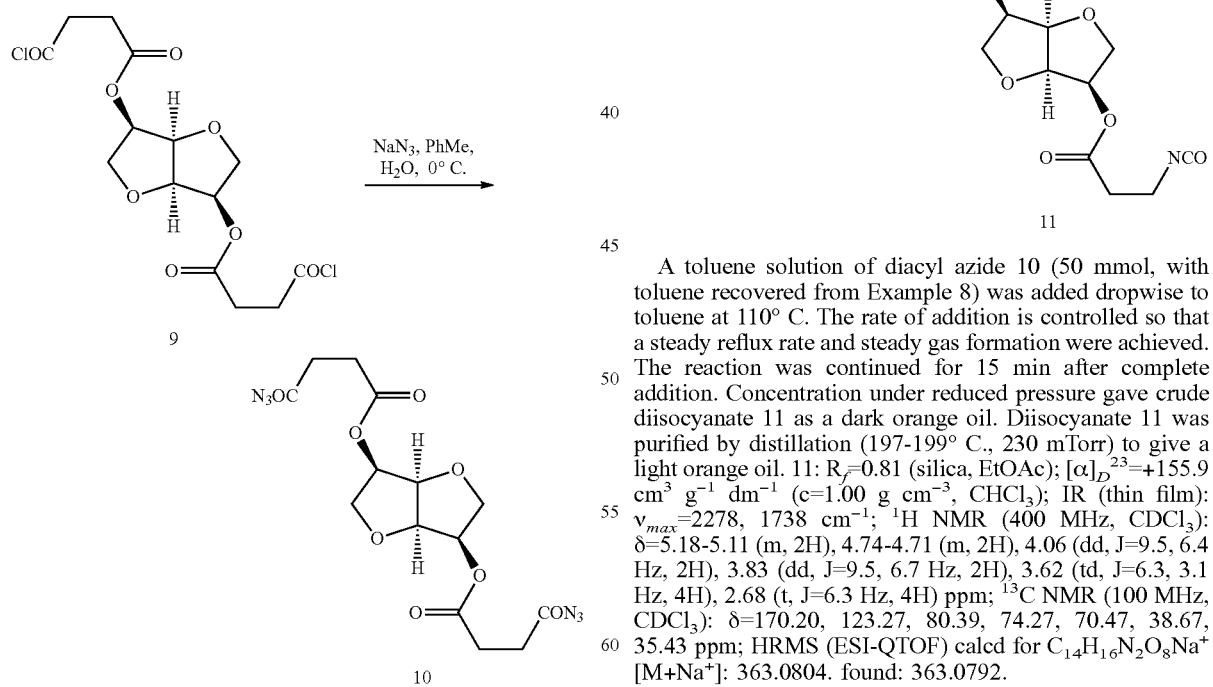

A toluene solution of diacyl azide 10 (50 mmol, with toluene recovered from Example 8) was added dropwise to toluene at 110° C. The rate of addition is controlled so that a steady reflux rate and steady gas formation were achieved. The reaction was continued for 15 min after complete addition. Concentration under reduced pressure gave crude diisocyanate 11 as a dark orange oil. Diisocyanate 11 was purified by distillation (197-199° C., 230 mTorr) to give a light orange oil. 11: $R_f$=0.81 (silica, EtOAc); $[α]_D^{23}$=+155.9 cm$^3$ g$^{-1}$ dm$^{-1}$ (c=1.00 g cm$^{-3}$, CHCl$_3$); IR (thin film): $ν_{max}$=2278, 1738 cm$^{-1}$; $^1$H NMR (400 MHz, CDCl$_3$): δ=5.18-5.11 (m, 2H), 4.74-4.71 (m, 2H), 4.06 (dd, J=9.5, 6.4 Hz, 2H), 3.83 (dd, J=9.5, 6.7 Hz, 2H), 3.62 (td, J=6.3, 3.1 Hz, 4H), 2.68 (t, J=6.3 Hz, 4H) ppm; $^{13}$C NMR (100 MHz, CDCl$_3$): δ=170.20, 123.27, 80.39, 74.27, 70.47, 38.67, 35.43 ppm; HRMS (ESI-QTOF) calcd for C$_{14}$H$_{16}$N$_2$O$_8$Na$^+$ [M+Na$^+$]: 363.0804. found: 363.0792.

Example 10 (Hypothetical). Synthesis of Diisocyanate 11

As illustrated in Scheme 11, diisocyanate 11 is synthesized from diacid chloride 9.

Scheme 11. Synthesis of diisocyanate 11.

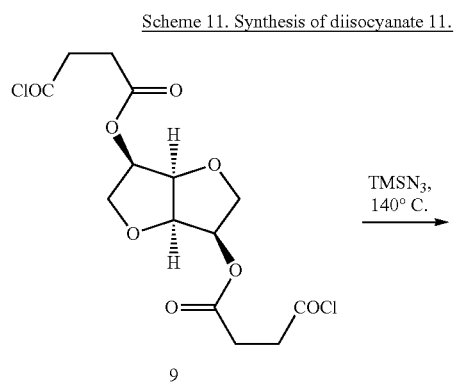

Trimethylsilyl azide (6 equiv) is added dropwise to diacid chloride 9 (1.92 g, 5 mmol) at 140° C., resulting in vigorous gas evolution. The reaction is continued at 140° C. for 30 min after complete addition. Concentration under reduced pressure gives crude diisocyanate 11 as a dark red oil. The chemical yield of diisocyanate 11 from isomannide (7) is estimated by $^1$H NMR analysis.
Isoidide-Derived Diisocyanate.

Example 11 (Hypothetical). Synthesis of Diacid 13

As illustrated in Scheme 12, diacid 13 is synthesized from isoidide 12 and succinic anhydride 2.

Scheme 12. Synthesis of diacid 13.

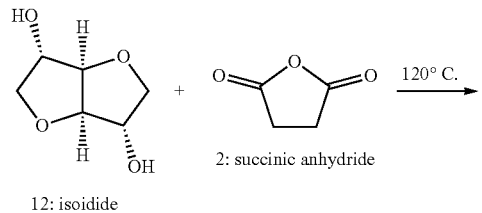

A mixture of isoidide (12, 1 equiv) and succinic anhydride (2, 2.3 equiv) is heated at 120° C. for 24 hr to give diacid 13. To avoid sublimation of succinic anhydride 2, the entire reaction vessel can be heated. The chemical yield is estimated by $^1$H NMR analysis. Sublimation of succinic anhydride (2) from the crude material affords a sample of diacid 13 for analysis.

Example 12 (Hypothetical). Synthesis of Diacid Chloride 14

As illustrated in Scheme 13, diacid chloride 14 is synthesized from diacid 13.

Scheme 13. Synthesis of diacid chloride 14.

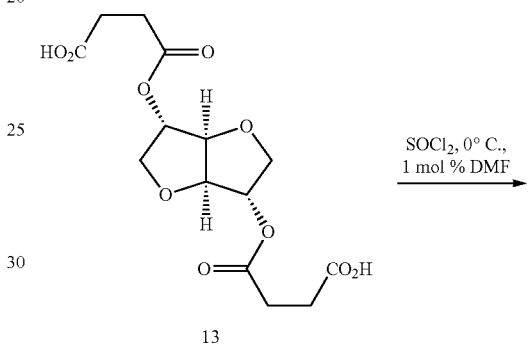

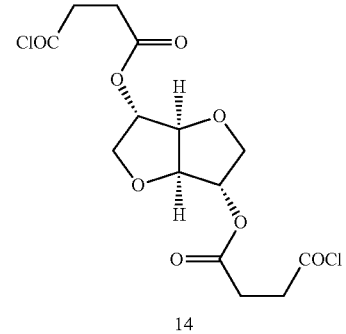

To a solution of crude diacid 13 (1 equiv) in thionyl chloride at 0° C. is added dimethylformamide (0.01 equiv). Vigorous gas evolution is observed for approximately 30 min. After another 1.5 hr, excess thionyl chloride is distilled out under reduced pressure (30° C.) to give diacid chloride 14. The chemical yield is estimated by $^1$H NMR analysis. A sample of diacid chloride 14 for analysis is obtained by the reaction of a purified sample of diacid 13.

Example 13 (Hypothetical). Synthesis of Diacyl Azide 15

As illustrated in Scheme 14, diacyl azide 15 is synthesized from diacid chloride 14.

Scheme 14. Synthesis of diacyl azide 15.

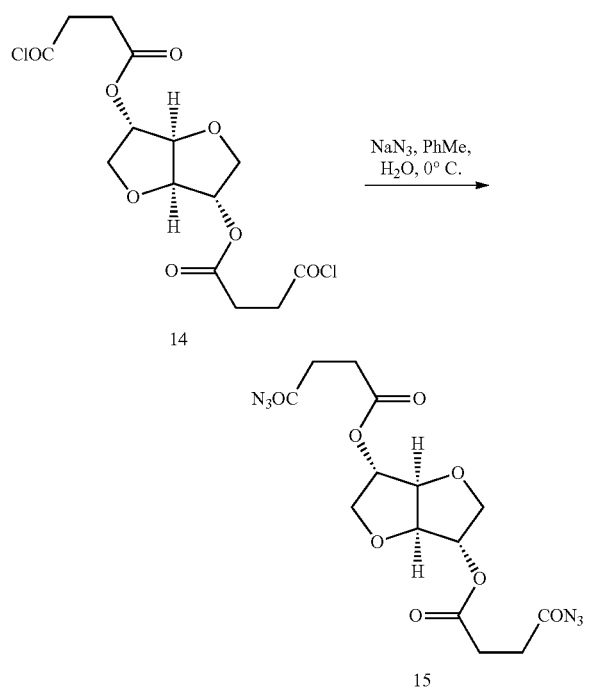

A solution of crude diacid chloride 14 (1 equiv) in toluene is added dropwise to an aqueous solution of sodium azide (5 equiv) at 0° C. The rate of addition is controlled so that the internal temperature of the reaction does not exceed 3° C. The reaction is continued at 0° C. for 20 min after complete addition. The reaction mixture is partitioned into two phases, and the organic phase is washed once with 10% potassium carbonate solution, once with water, and twice with brine, then dried over $Na_2SO_4$. Diacyl azide 15 is not concentrated due to its instability in pure form. The chemical yield of diacyl azide 15 from isoidide (12) is estimated by $^1$H NMR analysis of the crude material.

Example 14 (Hypothetical). Synthesis of Diisocyanate 16

As illustrated in Scheme 15, diisocyanate 16 is synthesized from diacyl azide 15.

Scheme 15. Synthesis of diisocyanate 16.

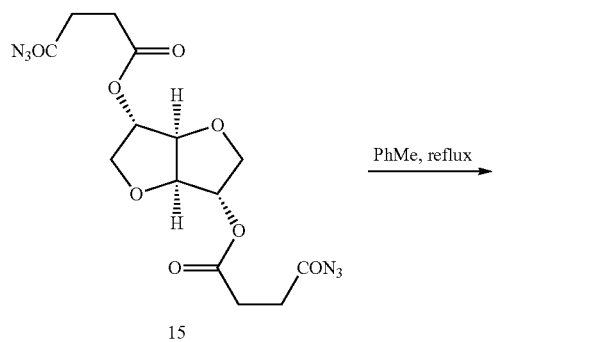

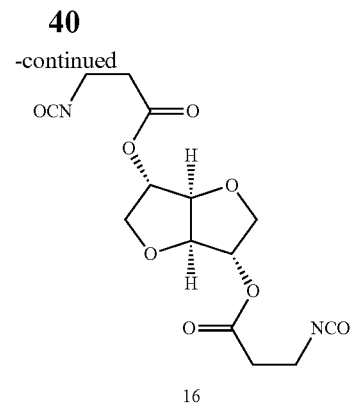

A toluene solution of diacyl azide 15 (with toluene recovered from Example 13) is added dropwise to toluene at 110° C. The rate of addition is controlled so that a steady reflux rate and steady gas formation are achieved. The reaction is continued for 15 min after complete addition. Concentration under reduced pressure gives crude diisocyanate 16 as a dark orange oil. Diisocyanate 16 is purified by distillation to give a light orange oil.

Example 15 (Hypothetical). Synthesis of Diisocyanate 16

As illustrated in Scheme 16, diisocyanate 16 is synthesized from diacid chloride 14.

Scheme 16. Synthesis of diisocyanate 16.

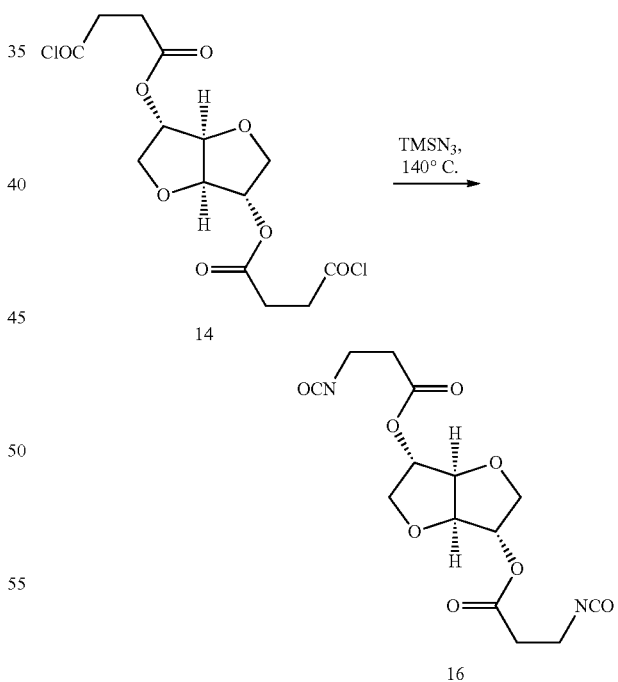

Trimethylsilyl azide (6 equiv) is added dropwise to diacid chloride 14 (1.92 g, 5 mmol) at 140° C., resulting in vigorous gas evolution. The reaction is continued at 140° C. for 30 min after complete addition. Concentration under reduced pressure gives crude diisocyanate 16 as a dark red oil. The chemical yield of diisocyanate 16 from isoidide (12) is estimated by $^1$H NMR analysis.

Synthesis of Polyurethanes

Example 16. Synthesis of Polyurethane

As illustrated in Scheme 17, polyurethane 18a was synthesized from diol 1 and diisocyanate 6.

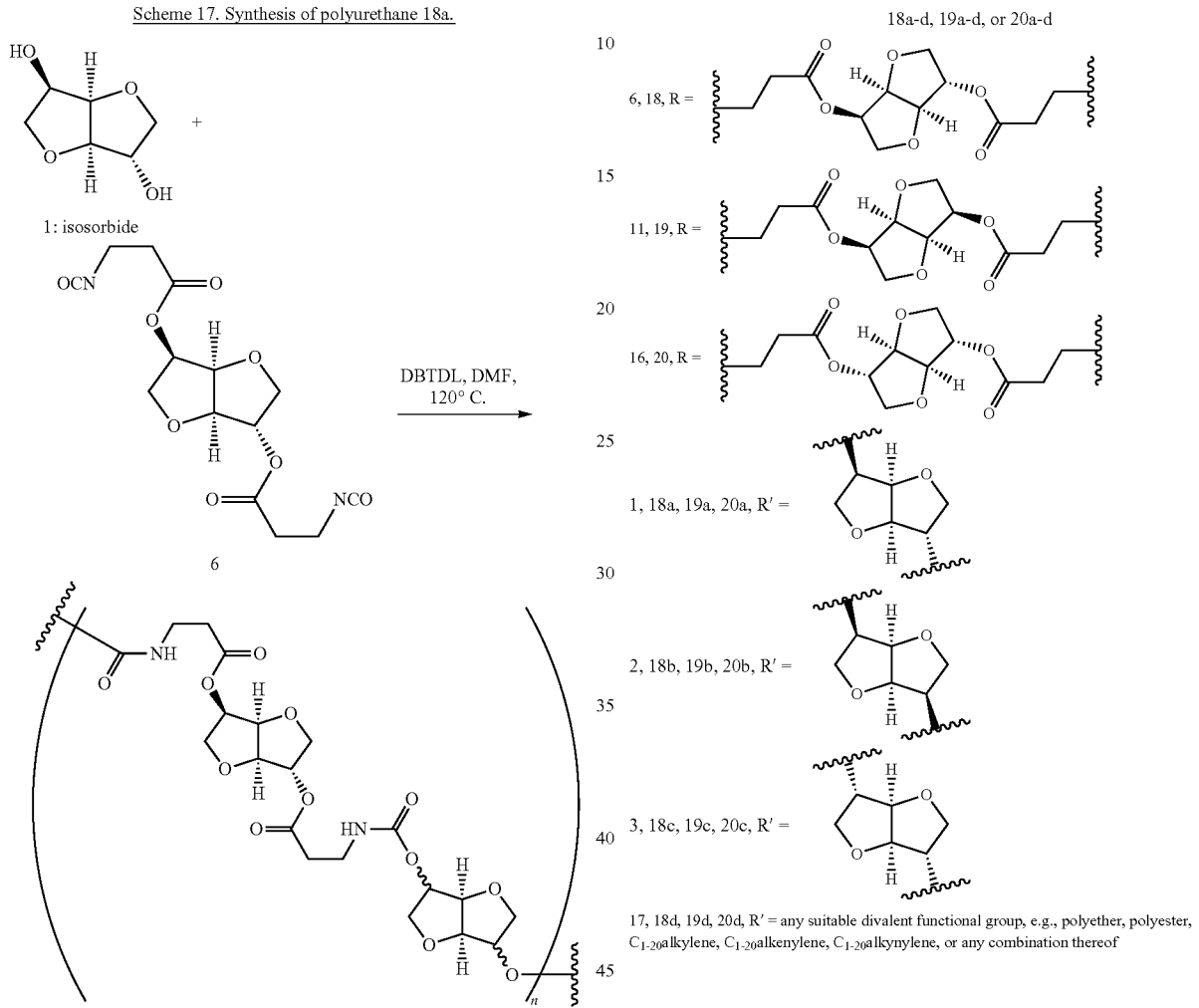

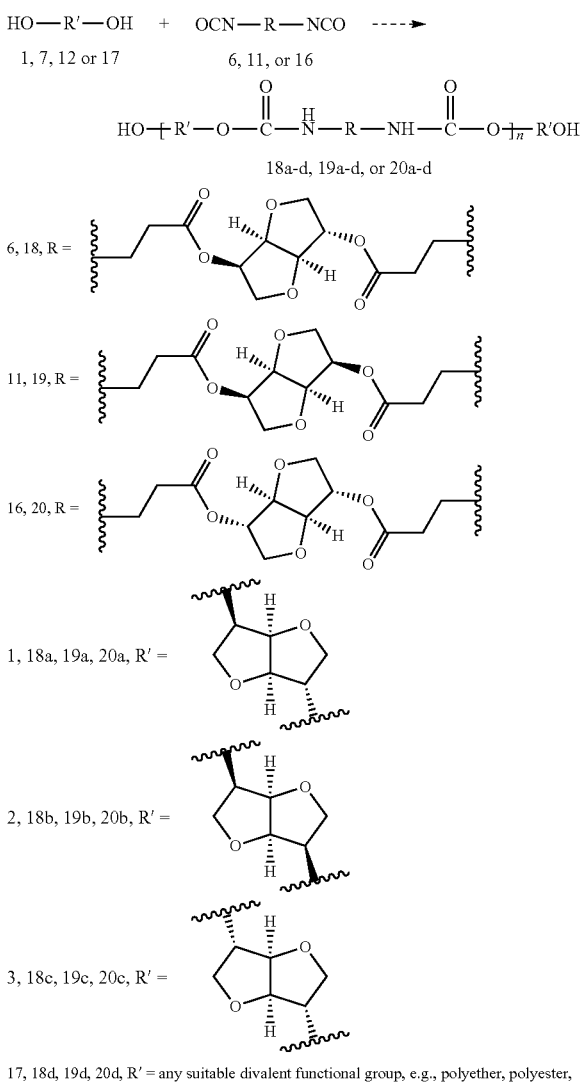

Diisocyanate 6 (1.52 g, 4.45 mmol), isosorbide (1, 620 mg, 4.24 mmol) and DMF (4 mL) were stirred over activated and powdered 4 Å molecular sieves for 30 min. Dibutyl tin laurate (DBTDL, ca. 10 µL) was added, and the reaction mixture was heated at 120° C. for 18 hr. The reaction was filtered into methanol (50 mL), and the resultant white precipitate was collected. Polyurethane 18a was dried at 50° C. under reduced pressure to yield an orange solid (1.08 g, 52.4% yield). 7: DSC (10° C./min): $T_g$=63.9° C., $T_m$=123.2° C., $T_d$=215.0° C.; GPC (DMF): $M_n$=5,147 g mol$^{-1}$, $M_w$=9,177 g mol$^{-1}$, $M_w/M_n$=1.78; TGA: $T_d$=200° C.

Example 17 (Hypothetical). Synthesis of Polyurethanes

As illustrated in Scheme 18 and Table 1, diisocyanates 6, 11, 16 are used to synthesize polyurethanes 18a-d, 19a-d, and 20a-d using polyols 1, 7, 12, or 17.

TABLE 1

| Reactions performed in Scheme 18. | | |
|---|---|---|
| Polyol | Diisocyanate | Polyurethane |
| 1 | 6 | 18a |
| 7 | 6 | 18b |
| 12 | 6 | 18c |
| 17 | 6 | 18d |
| 1 | 11 | 19a |
| 7 | 11 | 19b |
| 12 | 11 | 19c |
| 17 | 11 | 19d |
| 1 | 16 | 20a |
| 7 | 16 | 20b |
| 12 | 16 | 20c |
| 17 | 16 | 20d |

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

Additional Embodiments

The present invention provides for the following exemplary embodiments, the numbering of which is not to be construed as designating levels of importance:

Embodiment 1 provides a compound of Formula (I):

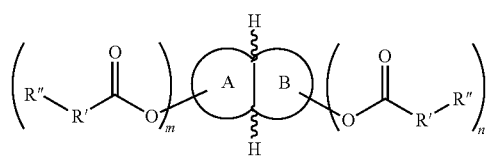

wherein fused rings A and B are each independently selected from ($C_5$-$C_{10}$)cycloalkyl and ($C_2$-$C_{10}$)heterocyclyl; m and n are each independently 1-8; R' is selected from the group consisting of ($C_2$-$C_{10}$)alkanylene, ($C_2$-$C_{10}$)alkenylene, and ($C_2$-$C_{10}$)alkynylene, wherein R' is unsubstituted or substituted with at least one J; R" is selected from the group consisting of —C(O)OH, —C(O)O⁻X⁺, —C(O)F, —C(O)Cl, —C(O)Br, —C(O)I, —C(O)$N_3$, and —NCO, wherein $X^+$ is a counterion; fused rings A and B are each independently unsubstituted or substituted with at least one of J, ($C_1$-$C_{10}$)alkyl, ($C_2$-$C_{10}$)alkenyl, ($C_2$-$C_{10}$)alkynyl, ($C_1$-$C_{10}$)haloalkyl, ($C_1$-$C_{10}$)alkoxy, ($C_1$-$C_{10}$)haloalkoxy, ($C_1$-$C_{10}$)cycloalkyl($C_0$-$C_{10}$)alkyl, ($C_1$-$C_{10}$)heterocyclyl($C_0$-$C_{10}$)alkyl, ($C_1$-$C_{10}$)aryl($C_0$-$C_{10}$)alkyl, or ($C_1$-$C_{10}$)heteroaryl($C_0$-$C_{10}$)alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J; and wherein J independently at each occurrence is selected from the group consisting of F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, C(O)$CH_2$C(O)R, C(S)R, C(O)OR, OC(O)R, OC(O)OR, C(O)$N(R)_2$, OC(O)$N(R)_2$, C(S)N$(R)_2$, $(CH_2)_{0-2}$NHC(O)R, N(R)N(R)C(O)R, N(R)N(R)C(O)OR, N(R)N(R)C(O)$N(R)_2$, N(R)$SO_2$R, N(R)$SO_2N(R)_2$, N(R)C(O)OR, N(R)C(O)R, N(R)C(S)R, N(R)C(O)$N(R)_2$, N(R)C(S)$N(R)_2$, N(C(O)R)C(O)R, N(OR)R, C(=NH)$N(R)_2$, C(O)N(OR)R, and C(=NOR)R, wherein R is independently at each occurrence selected from the group consisting of hydrogen, ($C_1$-$C_{10}$)alkyl, ($C_1$-$C_{10}$)cycloalkyl, ($C_1$-$C_{10}$)cycloalkyl($C_1$-$C_{10}$)alkyl, ($C_1$-$C_{10}$)aryl, ($C_1$-$C_{10}$)aralkyl, ($C_1$-$C_{10}$)heterocyclyl, ($C_1$-$C_{10}$)heterocyclyl($C_1$-$C_{10}$)alkyl, ($C_1$-$C_{10}$)heteroaryl, and ($C_1$-$C_{10}$)heteroaryl($C_1$-$C_{10}$)alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

Embodiment 2 provides the compound of Embodiment 1, wherein R" is —NCO.

Embodiment 3 provides the compound of any one of Embodiments 1-2, wherein R' is unsubstituted.

Embodiment 4 provides the compound of any one of Embodiments 1-3, wherein R' is —$CH_2$—$CH_2$—.

Embodiment 5 provides the compound of any one of Embodiments 1-4, wherein rings A and B are unsubstituted with the exception of the ester substituents including R' and R".

Embodiment 6 provides the compound of any one of Embodiments 1-5, wherein m=n=1, and one of the ester substituents including R' and R" is alpha to at least one carbon atom shared by rings A and B.

Embodiment 7 provides the compound of any one of Embodiments 1-6, wherein rings A and B are the same size.

Embodiment 8 provides the compound of any one of Embodiments 1-7, wherein rings A and B are 5-membered rings.

Embodiment 9 provides the compound of any one of Embodiments 1-8, wherein at least one of rings A and B include at least one oxygen atom.

Embodiment 10 provides the compound of any one of Embodiments 1-9, wherein each of rings A and B include at least one oxygen atom.

Embodiment 11 provides the compound of any one of Embodiments 1-10, wherein each of rings A and B is a tetrahydrofuran ring, wherein each carbon atom shared by rings A and B has an oxygen atom alpha thereto.

Embodiment 12 provides the compound of any one of Embodiments 1-1, wherein each of the two hydrogen atoms on the carbon atoms shared by rings A and B have syn stereochemistry with respect to one another.

Embodiment 13 provides the compound of any one of Embodiments 1-12, wherein m=n.

Embodiment 14 provides the compound of any one of Embodiments 1-13, wherein m=n=1.

Embodiment 15 provides the compound of Embodiment 14, wherein each of the two ester substituents including R' and R" are alpha to a different carbon atom shared by each of rings A and B.

Embodiment 16 provides the compound of Embodiment 1, wherein the compound is

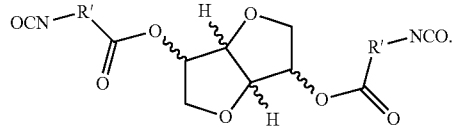

Embodiment 17 provides the compound of Embodiment 1, wherein the compound is

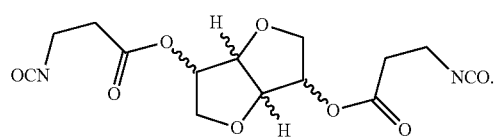

Embodiment 18 provides the compound of Embodiment 1, wherein the compound is

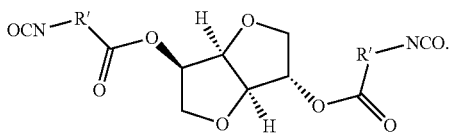

Embodiment 19 provides the compound of Embodiment 1, wherein the compound is

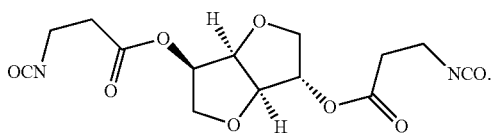

Embodiment 20 provides the compound of Embodiment 1, wherein the compound is

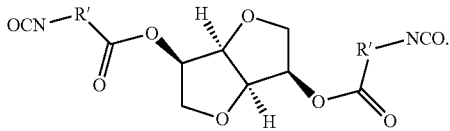

Embodiment 21 provides the compound of Embodiment 1, wherein the compound is

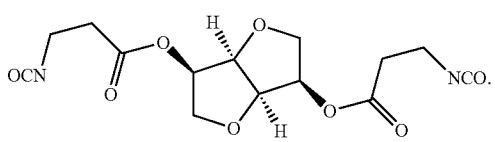

Embodiment 22 provides the compound of Embodiment 1, wherein the compound is

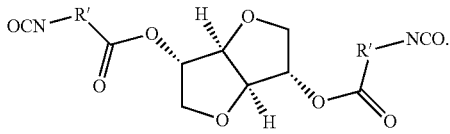

Embodiment 23 provides the compound of Embodiment 1, wherein the compound is

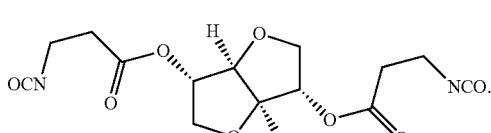

Embodiment 24 provides a method of making a polyisocyanate, comprising: a) contacting a compound having the structure

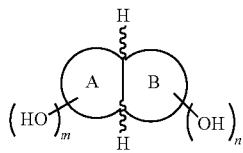

and an acid anhydride having the structure

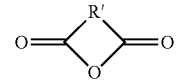

to provide a polyacid having the structure of Formula (I)

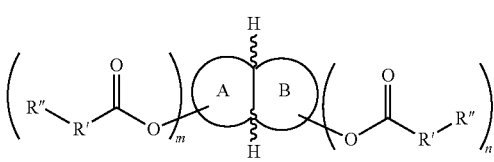

wherein R" is —C(O)OH; b) contacting the polyacid and an acyl halide generator, to provide a polyacyl halide having the structure of Formula (I) wherein R" is —C(O)X, wherein X is halide; and c) contacting the polyacyl halide and an azide generator, under conditions suitable to yield a polyisocyanate having the structure of Formula (I) wherein R" is —NCO; wherein fused rings A and B are each independently selected from $(C_5-C_{10})$cycloalkyl and $(C_2-C_{10})$heterocyclyl, m and n are each independently 1-8. R' is selected from the group consisting of $(C_2-C_{10})$alkanylene, $(C_2-C_{10})$alkenylene, and $(C_2-C_{10})$alkynylene, wherein R' is unsubstituted or substituted with at least one J, and fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J, and wherein J independently at each occurrence is selected from the group consisting of F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-2}NHC(O)R$, N(R)N(R)C(O)R, N(R)N(R)C(O)OR, $N(R)N(R)C(O)N(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(C(O)R)C(O)R, N(OR)R, $C(=NH)N(R)_2$, C(O)N(OR)R, and C(=NOR)R, wherein R is independently at each occurrence selected from the group consisting of hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

Embodiment 25 provides the method of Embodiment 24, wherein m=n=1.

Embodiment 26 provides the method of any one of Embodiments 24-25, wherein the acid anhydride is succinic anhydride.

Embodiment 27 provides the method of any one of Embodiments 24-26, wherein the acyl halide generator is at least one of thionyl chloride, thionyl bromide, phosphorous pentachloride, phosphorus pentabromide, cyanuric fluoride, phosgene, diphosgene, triphosgene, oxalyl chloride, phosphorus tribromide, phosphorus trichloride, and phosphoryl chloride.

Embodiment 28 provides the method of any one of Embodiments 24-27, wherein the azide generator is at least one of sodium azide, trimethylsilyl azide, triethylsilyl azide, lithium azide, potassium azide, tetrabutylammonium azide, tert-butyldimethylsilyl azide, and tert-butyldiphenylsilyl azide.

Embodiment 29 provides the method of any one of Embodiments 24-28, wherein contacting the polyacyl halide with an azide generator provides a polyacyl azide having the structure of Formula (I) wherein R''=—C(O)N$_3$, wherein the polyacyl azide undergoes a Curtius rearrangement to provide the polyisocyanate.

Embodiment 30 provides the method of any one of Embodiments 24-29, wherein the contacting the polyacyl halide and the azide generator is performed in a biphasic solution comprising at least an aqueous phase and an organic phase and optionally further comprising a phase transfer catalyst.

Embodiment 31 provides a polyurethane derived from the compound of any one of Embodiments 1-23.

Embodiment 32 provides a polyurethane comprising a reaction product of the polyisocyanate of any one of Embodiments 1-23 with R''=—NCO and an alcohol.

Embodiment 33 provides the polyurethane of Embodiment 32, wherein the alcohol comprises a polyol comprising a polyether polyol, a polyester polyol, or a combination thereof.

Embodiment 34 provides a method of making a polyurethane comprising contacting the polyisocyanate of any one of Embodiments 1-23 with R''=—NCO with an alcohol to provide a polyurethane.

Embodiment 35 provides the polyurethane of Embodiment 34, wherein the alcohol comprises a polyol comprising a polyether polyol, a polyester polyol, or a combination thereof.

Embodiment 36 provides a polyurethane comprising a plurality of subunits each having the structure of Formula (II)

(II)

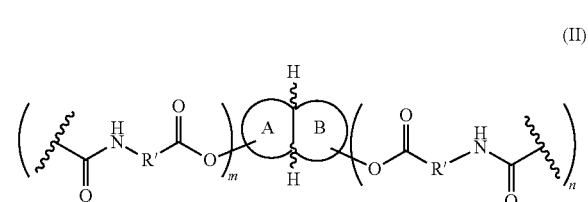

wherein fused rings A and B are each independently selected from (C$_5$-C$_{10}$)cycloalkyl and (C$_2$-C$_{10}$)heterocyclyl; m and n are each independently 1-8; R' is selected from the group consisting of (C$_2$-C$_{10}$)alkanylene, (C$_2$-C$_{10}$)alkenylene, and (C$_2$-C$_{10}$)alkynylene, wherein R' is unsubstituted or substituted with at least one J; fused rings A and B are each independently unsubstituted or substituted with at least one of J, (C$_1$-C$_{10}$)alkyl, (C$_2$-C$_{10}$)alkenyl, (C$_2$-C$_{10}$)alkynyl, (C$_1$-C$_{10}$)haloalkyl, (C$_1$-C$_{10}$)alkoxy, (C$_1$-C$_{10}$)haloalkoxy, (C$_1$-C$_{10}$)cycloalkyl(C$_0$-C$_{10}$)alkyl, (C$_1$-C$_{10}$)heterocyclyl(C$_0$-C$_0$)alkyl, (C$_1$-C$_{10}$)aryl(C$_0$-C$_{10}$)alkyl, or (C$_1$-C$_{10}$)heteroaryl(C$_0$-C$_{10}$)alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J; and wherein J independently at each occurrence is selected from the group consisting of F, Cl, Br, I, OR, CN, CF$_3$, OCF$_3$, R, O, S, C(O), S(O), methylenedioxy, ethylenedioxy, N(R)$_2$, SR, S(O)R, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-2}$NHC(O)R, N(R)N(R)C(O)R, N(R)N(R)C(O)OR, N(R)N(R)C(O)N(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(C(O)R)C(O)R, N(OR)R, C(=NH)N(R)$_2$, C(O)N(OR)R, and C(=NOR)R, wherein R is independently at each occurrence selected from the group consisting of hydrogen, (C$_1$-C$_{10}$)alkyl, (C$_1$-C$_{10}$)cycloalkyl, (C$_1$-C$_{10}$)cycloalkyl(C$_1$-C$_{10}$)alkyl, (C$_1$-C$_{10}$)aryl, (C$_1$-C$_{10}$)aralkyl, (C$_1$-C$_{10}$)heterocyclyl, (C$_1$-C$_{10}$)heterocyclyl(C$_1$-C$_{10}$)alkyl, (C$_1$-C$_{10}$)heteroaryl, and (C$_1$-C$_{10}$)heteroaryl(C$_1$-C$_{10}$)alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

Embodiment 37 provides the polyurethane of Embodiment 36, wherein Formula (II) is:

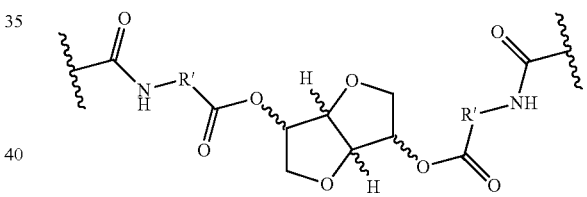

Embodiment 38 provides the polyurethane of Embodiment 36, wherein Formula (II) is:

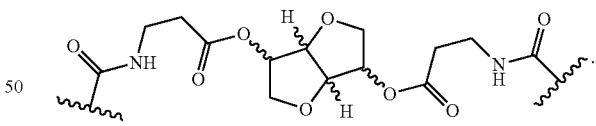

Embodiment 39 provides the polyurethane of Embodiment 36, wherein Formula (II) is:

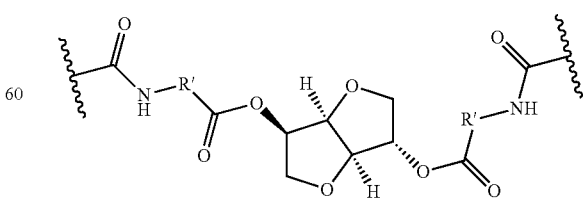

Embodiment 40 provides the polyurethane of Embodiment 36, wherein Formula (II) is:

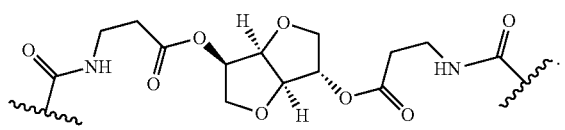 [SMILES: *C(=O)NCCC(=O)O[C@H]1CO[C@H]2[C@@H]1OC[C@H]2OC(=O)CCNC(*)=O]

Embodiment 41 provides the polyurethane of Embodiment 36, wherein Formula (II) is:

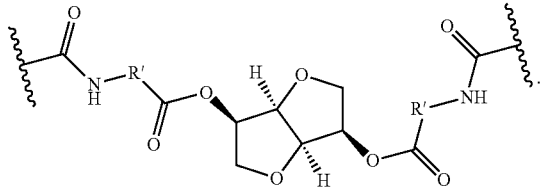

Embodiment 42 provides the polyurethane of Embodiment 36, wherein Formula (II) is:

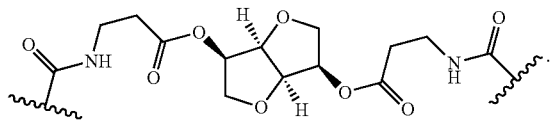 [SMILES: *C(=O)NCCC(=O)O[C@@H]1CO[C@H]2[C@@H]1OC[C@H]2OC(=O)CCNC(*)=O]

Embodiment 43 provides the polyurethane of Embodiment 36, wherein Formula (II) is:

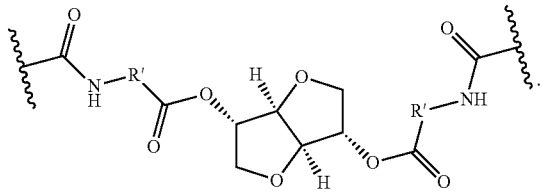

Embodiment 44 provides the polyurethane of Embodiment 36, wherein Formula (II) is:

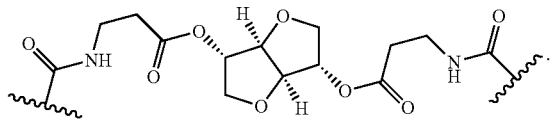 [SMILES: *C(=O)NCCC(=O)O[C@H]1CO[C@H]2[C@@H]1OC[C@@H]2OC(=O)CCNC(*)=O]

Embodiment 45 provides a aqueous dispersion comprising the polyurethane of any one of Embodiments 31-33 and 35-44.

Embodiment 46 provides the apparatus or method of any one or any combination of Embodiments 1-45 optionally configured such that all elements or options recited are available to use or select from.

We claim:
1. A method of making a polyisocyanate, comprising:
a) contacting
a compound having the structure

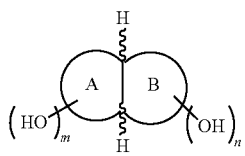

and
an acid anhydride having the structure

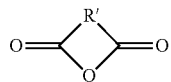

to provide a polyacid having the structure of Formula (I)

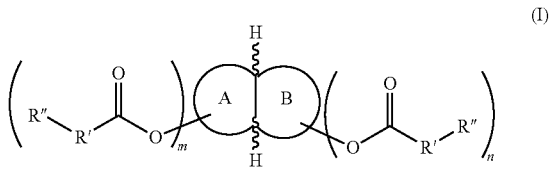

wherein R″ is —C(O)OH;
b) contacting the polyacid and an acyl halide generator, to provide a polyacyl halide having the structure of Formula (I) wherein R″ is —C(O)X, wherein X is halide; and
c) contacting the polyacyl halide and an azide generator, under conditions suitable to yield a polyisocyanate having the structure of Formula (I) wherein R″ is —NCO;
wherein fused rings A and B are each independently selected from $(C_5$-$C_{10})$cycloalkyl and $(C_2$-$C_{10})$heterocyclyl,
m and n are each independently 1-8,
R' is selected from the group consisting of $(C_2$-$C_{10})$alkanylene, $(C_2$-$C_{10})$alkenylene, and $(C_2$-$C_{10})$alkynylene, wherein R' is unsubstituted or substituted, and fused rings A and B are each independently unsubstituted or substituted.

2. The method of claim 1, wherein m=n=1.
3. The method of any one of claim 1, wherein the acid anhydride is succinic anhydride.
4. The method of any one of claim 1, wherein the acyl halide generator is at least one of thionyl chloride, thionyl bromide, phosphorous pentachloride, phosphorus pentabromide, cyanuric fluoride, phosgene, diphosgene, triphosgene, oxalyl chloride, phosphorus tribromide, phosphorus trichloride, and phosphoryl chloride.
5. The method of any one of claim 1, wherein the azide generator is at least one of sodium azide, trimethylsilyl azide, triethylsilyl azide, lithium azide, potassium azide, tetrabutylammonium azide, tert-butyldimethylsilyl azide, and tert-butyldiphenylsilyl azide.
6. The method of any one of claim 1, wherein contacting the polyacyl halide with an azide generator provides a polyacyl azide having the structure of Formula (I) wherein R″=—C(O)N$_3$, wherein the polyacyl azide undergoes a Curtius rearrangement to provide the polyisocyanate.
7. The method of any one of claim 1, wherein the contacting the polyacyl halide and the azide generator is performed in a biphasic solution comprising at least an aqueous phase and an organic phase and optionally further comprising a phase transfer catalyst.
8. The method of claim 1, wherein R' is unsubstituted.
9. The method of claim 1, wherein R' is —CH$_2$—CH$_2$—.
10. The method of claim 1, wherein rings A and B are unsubstituted with the exception of the ester substituents including R' and R″.
11. The method of claim 1, wherein m=n=1, and one of the ester substituents including R' and R″ is alpha to at least one carbon atom shared by rings A and B.
12. The method of claim 1, wherein each of rings A and B is a tetrahydrofuran ring, wherein each carbon atom shared by rings A and B has an oxygen atom alpha thereto.
13. The method of claim 1, wherein the polyisocyanate having the structure of Formula (I) is:

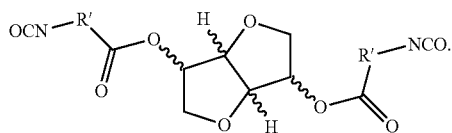

14. The method of claim 1, wherein the polyisocyanate having the structure of Formula (I) is:

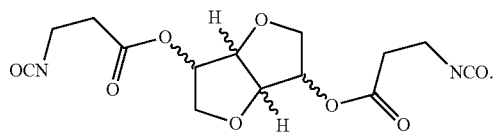

15. The method of claim 1, wherein the polyisocyanate having the structure of Formula (I) is:

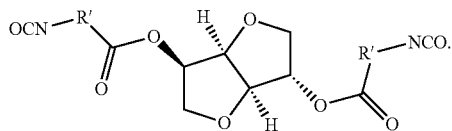

16. The method of claim 1, wherein the polyisocyanate having the structure of Formula (I) is:

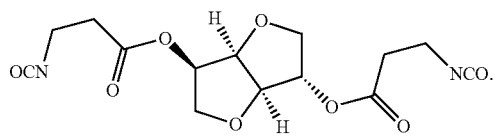

17. The method of claim 1, wherein the polyisocyanate having the structure of Formula (I) is:

18. The method of claim 1, wherein the polyisocyanate having the structure of Formula (I) is:

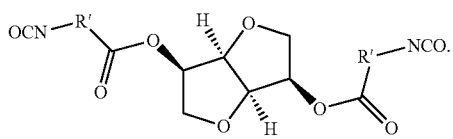

19. The method of claim 1, wherein the polyisocyanate having the structure of Formula (I) is:

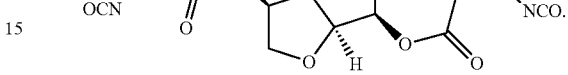

20. The method of claim 1, wherein e polyisocyanate having the structure of Formula (I) is:

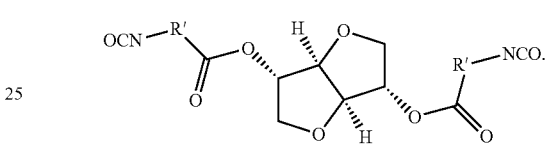

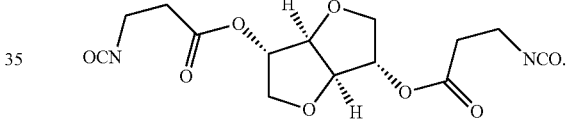

* * * * *

UNITED STATES PATENT AND TRADEMARK OFFICE
CERTIFICATE OF CORRECTION

PATENT NO. : 10,550,210 B2
APPLICATION NO. : 16/018148
DATED : February 4, 2020
INVENTOR(S) : Chen et al.

Page 1 of 2

It is certified that error appears in the above-identified patent and that said Letters Patent is hereby corrected as shown below:

On the Title Page

On page 2, in Column 1, item (56) under "Other Publications", Line 43, delete "filedJan." and insert --filed Jan.-- therefor In the Specification In Column 1, Line 21, delete "SAME.''" and insert --SAME,''-- therefor In Column 4, Line 42, delete "(II)." and insert --(II),-- therefor In Column 8, Line 42, delete "2,4-2,5-" and insert --2,4-, 2,5- -- therefor In Column 9, Line 15, delete "Ca-heterocyclyl" and insert --$C_4$-heterocyclyl-- therefor In Column 10, Line 6, delete "N-hydroxytetrazoyl," and insert --N-hydroxytetrazolyl,-- therefor In Column 12, Line 10, delete "moiety." and insert --moiety,-- therefor In Column 12, Line 54, delete "$(C_1-C_{10})$alkoxy." and insert --$(C_1-C_{10})$alkoxy,-- therefor In Column 13, Line 23, delete "m=n=1." and insert --m=n=1,-- therefor In Column 13, Line 46, delete "B." and insert --B,-- therefor In Column 14, Line 13, after "following", delete "system, having the"

In Column 21, Line 2, delete "min." and insert --min,-- therefor

Signed and Sealed this
Twenty-fourth Day of November, 2020

Andrei Iancu
*Director of the United States Patent and Trademark Office*

CERTIFICATE OF CORRECTION (continued)
U.S. Pat. No. 10,550,210 B2

In Column 21, Line 55, delete "min." and insert --min,-- therefor

In Column 25, Line 18, delete "($C_2$-$C_{10}$)alkynyl." and insert --($C_2$-$C_{10}$)alkynyl,-- therefor In Column 25, Line 19, delete "($C_1$-$C_{10}$)alkoxy." and insert --($C_1$-$C_{10}$)alkoxy,-- therefor In Column 25, Line 38, delete "($C_1$-$C_{10}$)aryl." and insert --($C_1$-$C_{10}$)aryl,-- therefor In Column 31, Line 34, delete "hr." and insert --hr,-- therefor In Column 43, Line 59, delete "($C_1$-$C_{10}$)aryl." and insert --($C_1$-$C_{10}$)aryl,-- therefor In the Claims In Column 50, Line 31, in Claim 3, after "method of", delete "any one of"

In Column 50, Line 33, in Claim 4, after "method of", delete "any one of"

In Column 50, Line 39, in Claim 5, after "method of", delete "any one of"

In Column 50, Line 44, in Claim 6, after "method of", delete "any one of"

In Column 50, Line 50, in Claim 7, after "method of", delete "any one of"

In Column 52, Line 29, in Claim 20, delete "e" and insert --the-- therefor